US008025695B2

(12) United States Patent
Fogarty et al.

(10) Patent No.: US 8,025,695 B2
(45) Date of Patent: *Sep. 27, 2011

(54) BIOLOGICALLY IMPLANTABLE HEART VALVE SYSTEM

(75) Inventors: Thomas J. Fogarty, Portola Valley, CA (US); Michael J. Drews, Sacramento, CA (US); Neil Holmgren, Alameda, CA (US); D. Bruce Modesitt, San Carlos, CA (US)

(73) Assignee: Medtronic, Inc., Minneapolis, MN (US)

( * ) Notice: Subject to any disclaimer, the term of this patent is extended or adjusted under 35 U.S.C. 154(b) by 60 days.

This patent is subject to a terminal disclaimer.

(21) Appl. No.: 10/355,429

(22) Filed: Jan. 31, 2003

(65) Prior Publication Data
US 2004/0122514 A1    Jun. 24, 2004

Related U.S. Application Data

(63) Continuation of application No. 10/327,821, filed on Dec. 20, 2002.

(51) Int. Cl.
*A61F 2/24* (2006.01)
(52) U.S. Cl. ............... 623/2.38; 623/2.14; 623/2.18
(58) Field of Classification Search .......... 623/2.13, 623/2.14, 2.38, 2.4, 2.41, 2.15, 2.18, 2.19
See application file for complete search history.

(56) References Cited

U.S. PATENT DOCUMENTS

| | | | | |
|---|---|---|---|---|
| 1,023,184 A | * | 4/1912 | Watts et al. | 409/147 |
| 1,124,025 A | * | 1/1915 | Johnson | 30/120 |
| 2,023,100 A | * | 12/1935 | Rose | 315/117 |
| 2,231,314 A | * | 2/1941 | Amour | 74/831 |
| 3,143,742 A | | 8/1964 | Cromie | |
| 3,320,974 A | | 5/1967 | High et al. | |
| 3,370,305 A | | 2/1968 | Goott et al. | |
| 3,371,352 A | | 3/1968 | Siposs | |
| 3,409,013 A | | 11/1968 | Berry | |
| 3,464,065 A | | 9/1969 | Cromie | |
| 3,546,710 A | | 12/1970 | Shumakov et al. | |
| 3,571,815 A | | 3/1971 | Somyk | |
| 3,574,865 A | * | 4/1971 | Hamaker | 623/2.34 |
| 3,628,535 A | | 12/1971 | Ostrowsky et al. | |
| 3,686,740 A | | 8/1972 | Shiley | |
| 3,691,567 A | * | 9/1972 | Cromie | 623/2.35 |
| 3,710,744 A | * | 1/1973 | Goodenough et al. | 112/470.14 |
| 3,744,060 A | | 7/1973 | Bellhouse et al. | |
| 3,755,823 A | * | 9/1973 | Hancock | 623/2.18 |
| 3,800,403 A | | 4/1974 | Anderson | |
| 3,839,741 A | * | 10/1974 | Haller | 623/2.34 |
| 3,959,827 A | | 6/1976 | Kaster | |
| 3,996,623 A | | 12/1976 | Kaster | |

(Continued)

FOREIGN PATENT DOCUMENTS

CN    2356656    1/2000

(Continued)

OTHER PUBLICATIONS

Merrian Webster Collegiate Dictionary 1633 (1998).*

(Continued)

*Primary Examiner* — Paul Prebilic

(57) ABSTRACT

A biologically implantable prosthesis is disclosed. The prosthesis can have a circumferentially expandable wall and elements that prevent the wall from collapsing once the wall is expanded. Methods of making and using the prosthesis are also disclosed.

37 Claims, 22 Drawing Sheets

U.S. PATENT DOCUMENTS

| | | | |
|---|---|---|---|
| 3,997,923 A * | 12/1976 | Possis | 623/2.4 |
| 4,035,849 A | 7/1977 | Angell et al. | |
| 4,078,268 A | 3/1978 | Possis | |
| 4,078,468 A | 3/1978 | Civitello | |
| 4,084,268 A | 4/1978 | Ionescu et al. | |
| 4,106,129 A | 8/1978 | Carpentier et al. | |
| 4,164,046 A * | 8/1979 | Cooley | 623/2.36 |
| 4,172,295 A | 10/1979 | Batten | |
| 4,211,325 A | 7/1980 | Wright | |
| 4,217,665 A | 8/1980 | Bex et al. | |
| 4,218,782 A | 8/1980 | Rygg | |
| 4,245,358 A | 1/1981 | Moasser | |
| 4,259,753 A | 4/1981 | Liotta et al. | |
| 4,291,420 A | 9/1981 | Reul | |
| 4,297,749 A | 11/1981 | Davis et al. | |
| RE30,912 E | 4/1982 | Hancock | |
| 4,343,048 A | 8/1982 | Ross et al. | |
| 4,364,126 A | 12/1982 | Rosen et al. | |
| 4,388,735 A | 6/1983 | Ionescu et al. | |
| 4,441,216 A * | 4/1984 | Ionescu et al. | 623/2.19 |
| 4,451,936 A * | 6/1984 | Carpentier et al. | 623/2.4 |
| 4,470,157 A | 9/1984 | Love | |
| 4,477,930 A * | 10/1984 | Totten et al. | 623/2.15 |
| 4,485,816 A | 12/1984 | Krumme | |
| 4,501,030 A | 2/1985 | Lane | |
| 4,506,394 A | 3/1985 | Bedard | |
| 4,535,483 A * | 8/1985 | Klawitter et al. | 623/2.4 |
| 4,548,202 A | 10/1985 | Duncan | |
| 4,605,407 A | 8/1986 | Black et al. | |
| 4,626,255 A | 12/1986 | Reichart et al. | |
| 4,629,459 A | 12/1986 | Ionescu et al. | |
| 4,665,906 A | 5/1987 | Jervis | |
| 4,666,442 A | 5/1987 | Arru et al. | |
| 4,680,031 A * | 7/1987 | Alonso | 623/2.13 |
| 4,683,883 A * | 8/1987 | Martin | 606/1 |
| 4,687,483 A * | 8/1987 | Fisher et al. | 623/2.14 |
| 4,692,164 A | 9/1987 | Dzemeshkevich et al. | |
| 4,702,250 A | 10/1987 | Ovil et al. | |
| 4,705,516 A * | 11/1987 | Barone et al. | 623/2.39 |
| 4,725,274 A * | 2/1988 | Lane et al. | 623/2.18 |
| 4,731,074 A | 3/1988 | Rousseau et al. | |
| 4,743,253 A | 5/1988 | Magladry | |
| 4,758,151 A | 7/1988 | Arru et al. | |
| 4,775,378 A | 10/1988 | Knoch et al. | |
| 4,778,461 A | 10/1988 | Pietsch et al. | |
| 4,790,843 A * | 12/1988 | Carpentier et al. | 623/2.39 |
| 4,816,029 A * | 3/1989 | Penny et al. | 623/2.19 |
| 4,851,000 A | 7/1989 | Gupta | |
| 4,865,600 A | 9/1989 | Carpentier et al. | |
| 4,888,009 A | 12/1989 | Lederman et al. | |
| 4,892,541 A * | 1/1990 | Alonso | 72/199 |
| 4,917,097 A | 4/1990 | Proudian et al. | |
| 4,917,698 A * | 4/1990 | Carpentier et al. | 623/2.36 |
| 4,935,030 A * | 6/1990 | Alonso | 623/2.22 |
| 4,960,424 A | 10/1990 | Grooters | |
| 4,993,428 A | 2/1991 | Arms | |
| 4,994,077 A | 2/1991 | Dobben | |
| 5,002,567 A | 3/1991 | Bona et al. | |
| 5,010,892 A | 4/1991 | Colvin et al. | |
| 5,032,128 A | 7/1991 | Alonso | |
| 5,035,708 A | 7/1991 | Alchas et al. | |
| 5,037,434 A | 8/1991 | Lane | |
| 5,071,431 A | 12/1991 | Sauter et al. | |
| 5,104,406 A | 4/1992 | Curcio et al. | |
| 5,147,391 A | 9/1992 | Lane | |
| 5,163,953 A | 11/1992 | Vince | |
| 5,163,954 A | 11/1992 | Curcio et al. | |
| 5,163,955 A | 11/1992 | Love et al. | |
| 5,178,633 A * | 1/1993 | Peters | 623/2.39 |
| 5,192,303 A | 3/1993 | Gatturna et al. | |
| 5,258,023 A | 11/1993 | Reger | |
| 5,316,016 A | 5/1994 | Adams et al. | |
| 5,326,370 A | 7/1994 | Love et al. | |
| 5,326,371 A | 7/1994 | Love et al. | |
| 5,332,402 A | 7/1994 | Teitelbaum | |
| 5,370,685 A * | 12/1994 | Stevens | 623/2.11 |
| 5,376,112 A | 12/1994 | Duran | |
| 5,396,887 A | 3/1995 | Imran | |
| 5,397,346 A | 3/1995 | Walker et al. | |
| 5,397,348 A | 3/1995 | Campbell et al. | |
| 5,397,351 A | 3/1995 | Pavcnik et al. | |
| 5,406,857 A | 4/1995 | Eberhardt et al. | |
| 5,411,552 A | 5/1995 | Andersen et al. | |
| 5,423,887 A | 6/1995 | Love et al. | |
| 5,425,741 A | 6/1995 | Lemp et al. | |
| 5,431,676 A | 7/1995 | Dubrul et al. | |
| 5,449,384 A | 9/1995 | Johnson | |
| 5,449,385 A | 9/1995 | Religa et al. | |
| 5,469,868 A | 11/1995 | Reger | |
| 5,476,510 A | 12/1995 | Eberhardt et al. | |
| 5,488,789 A | 2/1996 | Religa et al. | |
| 5,489,297 A * | 2/1996 | Duran | 623/2.13 |
| 5,489,298 A | 2/1996 | Love et al. | |
| 5,500,016 A | 3/1996 | Fisher | |
| 5,531,784 A | 7/1996 | Love et al. | |
| 5,533,515 A | 7/1996 | Coller et al. | |
| 5,549,665 A | 8/1996 | Vesely et al. | |
| 5,549,666 A * | 8/1996 | Hata et al. | 623/2.13 |
| 5,554,185 A * | 9/1996 | Block et al. | 623/2.12 |
| 5,562,729 A | 10/1996 | Purdy et al. | |
| 5,571,175 A * | 11/1996 | Vanney et al. | 623/2.41 |
| 5,571,215 A | 11/1996 | Sterman et al. | |
| 5,573,007 A | 11/1996 | Bobo | |
| 5,573,543 A | 11/1996 | Akopov et al. | |
| 5,578,076 A | 11/1996 | Krueger et al. | |
| 5,584,803 A | 12/1996 | Stevens et al. | |
| 5,607,470 A * | 3/1997 | Milo | 623/2.39 |
| 5,613,982 A | 3/1997 | Goldstein | |
| 5,618,307 A | 4/1997 | Donlon et al. | |
| 5,626,607 A | 5/1997 | Malecki et al. | |
| 5,628,789 A | 5/1997 | Vanney et al. | |
| 5,662,704 A * | 9/1997 | Gross | 623/2.1 |
| 5,669,917 A | 9/1997 | Sauer | |
| 5,693,090 A | 12/1997 | Unsworth et al. | |
| 5,695,503 A * | 12/1997 | Krueger et al. | 606/151 |
| 5,713,952 A | 2/1998 | Vanney et al. | |
| 5,713,953 A | 2/1998 | Vallana et al. | |
| 5,716,370 A * | 2/1998 | Williamson et al. | 606/153 |
| 5,716,399 A | 2/1998 | Love | |
| 5,720,755 A | 2/1998 | Dakov | |
| 5,725,554 A | 3/1998 | Simon | |
| 5,728,064 A | 3/1998 | Burns et al. | |
| 5,728,151 A | 3/1998 | Garrison et al. | |
| 5,735,894 A * | 4/1998 | Krueger et al. | 623/2.11 |
| 5,752,522 A | 5/1998 | Murphy | |
| 5,755,782 A | 5/1998 | Love et al. | |
| 5,766,240 A | 6/1998 | Johnson | |
| 5,776,187 A | 7/1998 | Krueger et al. | |
| 5,776,188 A | 7/1998 | Shepherd et al. | |
| 5,800,527 A | 9/1998 | Jansen et al. | |
| 5,807,405 A * | 9/1998 | Vanney et al. | 623/2.11 |
| 5,814,097 A | 9/1998 | Sterman et al. | |
| 5,814,098 A | 9/1998 | Hinnenkamp et al. | |
| 5,814,100 A | 9/1998 | Carpentier et al. | |
| 5,824,060 A * | 10/1998 | Christie et al. | 128/898 |
| 5,824,061 A * | 10/1998 | Quijano et al. | 623/1.13 |
| 5,824,064 A | 10/1998 | Taheri | |
| 5,830,239 A * | 11/1998 | Toomes | 8/94.11 |
| 5,840,081 A | 11/1998 | Andersen et al. | |
| 5,843,179 A * | 12/1998 | Vanney et al. | 623/2.38 |
| 5,848,969 A | 12/1998 | Panescu et al. | |
| 5,855,563 A | 1/1999 | Kaplan et al. | |
| 5,855,601 A | 1/1999 | Bessler et al. | |
| 5,855,603 A | 1/1999 | Reif | |
| 5,860,992 A | 1/1999 | Daniel | |
| 5,861,028 A * | 1/1999 | Angell | 623/2.11 |
| 5,865,801 A | 2/1999 | Houser | |
| 5,873,906 A | 2/1999 | Lau et al. | |
| 5,876,436 A * | 3/1999 | Vanney et al. | 623/2.39 |
| 5,879,371 A | 3/1999 | Gardiner et al. | |
| 5,891,160 A | 4/1999 | Williamson, IV et al. | |
| 5,891,195 A | 4/1999 | Klostermeyer et al. | |
| 5,895,420 A | 4/1999 | Mirsch, II et al. | |
| 5,902,308 A | 5/1999 | Murphy | |
| 5,908,450 A | 6/1999 | Gross et al. | |
| 5,908,452 A | 6/1999 | Bokros et al. | |
| 5,910,170 A | 6/1999 | Reimink et al. | |

| Patent No. | Kind | Date | Inventor | Ref |
|---|---|---|---|---|
| 5,919,147 | A | 7/1999 | Jain | |
| 5,921,934 | A | 7/1999 | Teo | |
| 5,921,935 | A | 7/1999 | Hickey | |
| 5,924,984 | A | 7/1999 | Rao | |
| 5,925,061 | A | 7/1999 | Ogi et al. | |
| 5,925,063 | A | 7/1999 | Khosravi | |
| 5,931,969 | A | 8/1999 | Carpentier et al. | |
| 5,935,163 | A | 8/1999 | Gabbay | |
| 5,957,940 | A | 9/1999 | Tanner et al. | |
| 5,957,949 | A | 9/1999 | Leonhardt et al. | |
| 5,961,549 | A | 10/1999 | Nguyen et al. | |
| 5,961,550 | A | 10/1999 | Carpentier et al. | |
| 5,972,004 | A | 10/1999 | Williamson, IV et al. | |
| 5,972,024 | A | 10/1999 | Northrup, III | |
| 5,976,183 | A | 11/1999 | Ritz | |
| 5,984,959 | A | 11/1999 | Robertson et al. | |
| 5,984,973 | A | 11/1999 | Girard et al. | |
| 6,007,577 | A | 12/1999 | Vanney et al. | |
| 6,010,531 | A | 1/2000 | Donlon et al. | |
| 6,042,607 | A | 3/2000 | Williamson, IV et al. | |
| 6,045,576 | A | 4/2000 | Starr et al. | |
| 6,059,827 | A * | 5/2000 | Fenton, Jr. | 623/2.17 |
| 6,066,160 | A | 5/2000 | Colvin et al. | |
| 6,068,657 | A | 5/2000 | Lapeyre et al. | |
| 6,074,041 | A | 6/2000 | Imanaka et al. | |
| 6,074,417 | A * | 6/2000 | Peredo | 623/2.1 |
| 6,074,418 | A * | 6/2000 | Buchanan et al. | 623/2.11 |
| 6,081,737 | A | 6/2000 | Shah | |
| 6,083,179 | A | 7/2000 | Oredsson | |
| 6,096,074 | A | 8/2000 | Pedros | |
| 6,099,475 | A | 8/2000 | Seward et al. | |
| 6,102,944 | A | 8/2000 | Huynh et al. | |
| 6,106,550 | A * | 8/2000 | Magovern et al. | 623/2.38 |
| 6,110,200 | A | 8/2000 | Hinnenkamp | |
| 6,113,632 | A | 9/2000 | Reif | |
| 6,117,091 | A | 9/2000 | Young et al. | |
| 6,126,007 | A | 10/2000 | Kari et al. | |
| 6,129,758 | A | 10/2000 | Love | |
| 6,139,575 | A | 10/2000 | Shu et al. | |
| 6,143,024 | A | 11/2000 | Campbell et al. | |
| 6,143,025 | A * | 11/2000 | Stobie et al. | 623/2.39 |
| 6,149,658 | A | 11/2000 | Gardiner et al. | |
| 6,152,935 | A | 11/2000 | Kammerer et al. | |
| 6,162,233 | A | 12/2000 | Williamson, IV et al. | |
| 6,165,183 | A | 12/2000 | Kuehn et al. | |
| 6,168,614 | B1 * | 1/2001 | Andersen et al. | 623/1.26 |
| 6,176,877 | B1 | 1/2001 | Buchanan et al. | |
| 6,176,977 | B1 * | 1/2001 | Taylor et al. | 204/176 |
| 6,183,512 | B1 | 2/2001 | Howanec et al. | |
| 6,197,054 | B1 * | 3/2001 | Hamblin et al. | 623/2.38 |
| 6,200,306 | B1 | 3/2001 | Klostermeyer | |
| 6,203,553 | B1 | 3/2001 | Robertson | |
| 6,214,043 | B1 * | 4/2001 | Krueger et al. | 623/2.11 |
| 6,217,610 | B1 * | 4/2001 | Carpentier et al. | 623/2.37 |
| 6,217,611 | B1 | 4/2001 | Klostermeyer | |
| 6,231,561 | B1 | 5/2001 | Frazier | |
| 6,231,602 | B1 * | 5/2001 | Carpentier et al. | 623/2.36 |
| 6,241,765 | B1 | 6/2001 | Griffin et al. | |
| 6,245,102 | B1 | 6/2001 | Jayaraman | |
| 6,245,105 | B1 | 6/2001 | Nguyen et al. | |
| 6,254,636 | B1 * | 7/2001 | Peredo | 623/2.15 |
| 6,264,691 | B1 | 7/2001 | Gabbay | |
| 6,270,526 | B1 | 8/2001 | Cox | |
| 6,270,527 | B1 | 8/2001 | Campbell et al. | |
| 6,283,127 | B1 | 9/2001 | Sterman et al. | |
| 6,283,995 | B1 | 9/2001 | Moe et al. | |
| 6,287,339 | B1 * | 9/2001 | Vazquez et al. | 623/2.4 |
| 6,290,674 | B1 | 9/2001 | Roue et al. | |
| 6,299,638 | B1 | 10/2001 | Sauter | |
| 6,309,417 | B1 * | 10/2001 | Spence et al. | 623/2.11 |
| 6,312,447 | B1 | 11/2001 | Grimes | |
| 6,312,465 | B1 | 11/2001 | Griffin et al. | |
| 6,319,280 | B1 * | 11/2001 | Schoon | 623/2.11 |
| 6,319,281 | B1 * | 11/2001 | Patel | 623/2.3 |
| 6,322,588 | B1 | 11/2001 | Ogle et al. | |
| 6,328,727 | B1 | 12/2001 | Frazier et al. | |
| 6,328,763 | B1 * | 12/2001 | Love et al. | 623/2.15 |
| 6,334,446 | B1 | 1/2002 | Beyar | |
| 6,338,740 | B1 | 1/2002 | Carpentier | |
| 6,350,281 | B1 | 2/2002 | Rhee | |
| 6,358,278 | B1 | 3/2002 | Brendzel et al. | |
| 6,358,556 | B1 | 3/2002 | Ding et al. | |
| 6,371,983 | B1 * | 4/2002 | Lane | 623/2.14 |
| 6,391,053 | B1 * | 5/2002 | Brendzel et al. | 623/2.2 |
| 6,395,025 | B1 * | 5/2002 | Fordenbacher et al. | 623/2.28 |
| 6,402,780 | B2 | 6/2002 | Williamson, IV et al. | |
| 6,409,759 | B1 | 6/2002 | Peredo | |
| 6,413,275 | B1 | 7/2002 | Nguyen et al. | |
| 6,419,696 | B1 | 7/2002 | Ortiz et al. | |
| 6,425,916 | B1 | 7/2002 | Garrison et al. | |
| 6,440,164 | B1 | 8/2002 | DiMatteo et al. | |
| 6,447,524 | B1 | 9/2002 | Knodel | |
| 6,454,799 | B1 * | 9/2002 | Schreck | 623/2.18 |
| 6,458,153 | B1 | 10/2002 | Bailey et al. | |
| 6,461,382 | B1 * | 10/2002 | Cao | 623/2.19 |
| 6,468,305 | B1 * | 10/2002 | Otte | 623/2.4 |
| 6,503,272 | B2 | 1/2003 | Duerig et al. | |
| 6,514,265 | B2 | 2/2003 | Ho et al. | |
| 6,530,952 | B2 * | 3/2003 | Vesely | 623/2.18 |
| 6,547,827 | B2 | 4/2003 | Carpentier et al. | |
| 6,551,332 | B1 | 4/2003 | Nguyen et al. | |
| 6,558,418 | B2 | 5/2003 | Carpentier et al. | |
| 6,569,196 | B1 | 5/2003 | Vesely | |
| 6,582,462 | B1 | 6/2003 | Andersen et al. | |
| 6,585,766 | B1 | 7/2003 | Huynh et al. | |
| 6,589,279 | B1 | 7/2003 | Anderson et al. | |
| 6,598,307 | B2 | 7/2003 | Love et al. | |
| 6,602,289 | B1 | 8/2003 | Colvin et al. | |
| 6,607,541 | B1 | 8/2003 | Gardiner et al. | |
| 6,613,059 | B2 | 9/2003 | Ho et al. | |
| 6,613,085 | B1 | 9/2003 | Anderson et al. | |
| 6,641,593 | B1 | 11/2003 | Schaller et al. | |
| 6,652,578 | B2 | 11/2003 | Bailey et al. | |
| 6,660,032 | B2 | 12/2003 | Klumb et al. | |
| 6,676,671 | B2 | 1/2004 | Robertson et al. | |
| 6,678,862 | B1 | 1/2004 | Love et al. | |
| 6,682,559 | B2 | 1/2004 | Myers et al. | |
| 6,685,739 | B2 | 2/2004 | DiMatteo et al. | |
| 6,692,513 | B2 | 2/2004 | Streeter et al. | |
| 6,695,859 | B1 | 2/2004 | Golden et al. | |
| 6,709,457 | B1 | 3/2004 | Otte et al. | |
| 6,716,243 | B1 | 4/2004 | Colvin et al. | |
| 6,716,244 | B2 | 4/2004 | Klaco | |
| 6,716,789 | B1 | 4/2004 | Cox | |
| 6,719,790 | B2 | 4/2004 | Brendzel et al. | |
| 6,730,118 | B2 | 5/2004 | Spenser et al. | |
| 6,733,525 | B2 * | 5/2004 | Yang et al. | 623/2.18 |
| 6,764,508 | B1 | 7/2004 | Roehe et al. | |
| 6,767,362 | B2 | 7/2004 | Schreck | |
| 6,769,434 | B2 | 8/2004 | Liddicoat et al. | |
| 6,776,785 | B1 | 8/2004 | Yencho | |
| 6,786,924 | B2 | 9/2004 | Ryan et al. | |
| 6,786,925 | B1 | 9/2004 | Buchanan et al. | |
| 6,790,229 | B1 * | 9/2004 | Berreklouw | 623/2.1 |
| 6,790,230 | B2 | 9/2004 | Beyersdorf et al. | |
| 6,805,711 | B2 | 10/2004 | Quijano et al. | |
| 6,830,585 | B1 | 12/2004 | Artof et al. | |
| 6,833,924 | B2 | 12/2004 | Love et al. | |
| 6,846,324 | B2 | 1/2005 | Stobie | |
| 6,846,325 | B2 | 1/2005 | Liddicoat | |
| 6,873,902 | B2 | 1/2005 | Nguyen et al. | |
| 6,872,226 | B2 | 3/2005 | Cali et al. | |
| 6,893,459 | B1 | 5/2005 | Macoviak | |
| 6,893,460 | B2 | 5/2005 | Spenser et al. | |
| 6,896,690 | B1 | 5/2005 | Lambrecht et al. | |
| 6,908,481 | B2 | 6/2005 | Cribier | |
| 6,911,043 | B2 | 6/2005 | Myers et al. | |
| 6,913,607 | B2 | 7/2005 | Ainsworth et al. | |
| 6,918,917 | B1 | 7/2005 | Nguyen et al. | |
| 6,921,407 | B2 | 7/2005 | Nguyen et al. | |
| 6,926,730 | B1 | 8/2005 | Nguyen et al. | |
| 6,929,653 | B2 | 8/2005 | Strecter | |
| 6,939,365 | B1 | 9/2005 | Fogarty | |
| 6,945,980 | B2 | 9/2005 | Nguyen et al. | |
| 6,945,997 | B2 | 9/2005 | Huynh et al. | |
| 6,960,221 | B2 | 11/2005 | Ho et al. | |
| 7,011,681 | B2 | 3/2006 | Vesely | |
| 7,025,780 | B2 | 4/2006 | Gabbay | |

| Patent/Publication | Date | Name |
|---|---|---|
| 7,037,333 B2 | 5/2006 | Myers et al. |
| 7,070,616 B2 | 7/2006 | Majercak et al. |
| 7,083,648 B2 | 8/2006 | Yu |
| 7,097,659 B2 | 8/2006 | Woolfson et al. |
| 7,101,396 B2 | 9/2006 | Artof et al. |
| 7,134,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 | 2/2007 | Hill et al. |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,445,632 B2 | 11/2008 | McGuckin et al. |
| 7,513,909 B2 | 4/2009 | Lane et al. |
| 7,547,313 B2 | 6/2009 | Gardiner et al. |
| 7,556,647 B2 | 7/2009 | Drews et al. |
| 7,578,843 B2 | 8/2009 | Shu |
| 7,597,711 B2 * | 10/2009 | Drews et al. ............. 623/2.11 |
| 7,708,775 B2 | 5/2010 | Rowe et al. |
| 7,717,955 B2 * | 5/2010 | Lane et al. ............. 623/2.41 |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat et al. |
| 7,803,184 B2 | 9/2010 | McGuckin et al. |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044656 A1 * | 11/2001 | Williamson et al. ......... 623/2.11 |
| 2001/0049492 A1 | 12/2001 | Frazier et al. |
| 2002/0026238 A1 | 2/2002 | Lane et al. |
| 2002/0032480 A1 | 3/2002 | Spence et al. |
| 2002/0032481 A1 | 3/2002 | Gabbay |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 * | 6/2002 | Schwartz ............. 600/486 |
| 2002/0077698 A1 | 6/2002 | Peredo |
| 2002/0091441 A1 | 7/2002 | Nguyen, et al |
| 2002/0116054 A1 | 8/2002 | Lundell et al. |
| 2002/0123802 A1 * | 9/2002 | Snyders ............. 623/2.18 |
| 2002/0128684 A1 | 9/2002 | Foerster |
| 2002/0138138 A1 * | 9/2002 | Yang ............. 623/2.18 |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 * | 12/2002 | Klaco ............. 623/2.4 |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 * | 1/2003 | Moe et al. ............. 623/2.4 |
| 2003/0023303 A1 | 1/2003 | Palmaz et al. |
| 2003/0036791 A1 | 2/2003 | Bonhoeffer et al. |
| 2003/0036795 A1 | 2/2003 | Andersen et al. |
| 2003/0040792 A1 | 2/2003 | Gabbay |
| 2003/0045902 A1 | 3/2003 | Weadock |
| 2003/0050693 A1 | 3/2003 | Quijano et al. |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0136417 A1 * | 7/2003 | Fonseca et al. ............. 128/899 |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0199974 A1 | 10/2003 | Lee et al. |
| 2003/0229394 A1 | 12/2003 | Ogle et al. |
| 2003/0236568 A1 | 12/2003 | Hojeibane et al. |
| 2004/0015232 A1 * | 1/2004 | Shu et al. ............. 623/2.4 |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 | 3/2004 | Woolfson |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0106990 A1 | 6/2004 | Spence et al. |
| 2004/0122514 A1 | 6/2004 | Fogarty |
| 2004/0122516 A1 | 6/2004 | Fogarty |
| 2004/0122526 A1 | 6/2004 | Imran |
| 2004/0167573 A1 | 8/2004 | Williamson, IV et al. |
| 2004/0167620 A1 | 8/2004 | Ortiz et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |

| | | | | | | |
|---|---|---|---|---|---|---|
| 2005/0137694 A1 | 6/2005 | Haug et al. | | 2007/0142848 A1 | 6/2007 | Ainsworth et al. |
| 2005/0137695 A1 | 6/2005 | Salahieh et al. | | 2007/0142906 A1 | 6/2007 | Figulla et al. |
| 2005/0137696 A1 | 6/2005 | Salahieh et al. | | 2007/0142907 A1 | 6/2007 | Moaddeb et al. |
| 2005/0137702 A1 | 6/2005 | Haug et al. | | 2007/0150053 A1 | 6/2007 | Gurskis |
| 2005/0150775 A1 | 7/2005 | Zhang et al. | | 2007/0156233 A1 | 7/2007 | Kapadia et al. |
| 2005/0159811 A1 | 7/2005 | Lane | | 2007/0162103 A1 | 7/2007 | Case et al. |
| 2005/0165477 A1 | 7/2005 | Anduiza et al. | | 2007/0162107 A1 | 7/2007 | Haug et al. |
| 2005/0165479 A1 | 7/2005 | Lane | | 2007/0162111 A1 | 7/2007 | Fukamachi et al. |
| 2005/0182483 A1 | 8/2005 | Osborne et al. | | 2007/0162113 A1 | 7/2007 | Sharkawy et al. |
| 2005/0182486 A1 | 8/2005 | Gabbay | | 2007/0179604 A1 | 8/2007 | Lane |
| 2005/0192665 A1 | 9/2005 | Spenser et al. | | 2007/0185565 A1 | 8/2007 | Schwammenthal et al. |
| 2005/0203616 A1 | 9/2005 | Cribier | | 2007/0198097 A1 | 8/2007 | Zegdi |
| 2005/0203617 A1 | 9/2005 | Forster et al. | | 2007/0203575 A1 | 8/2007 | Forster et al. |
| 2005/0203618 A1 | 9/2005 | Sharkawy et al. | | 2007/0203576 A1 | 8/2007 | Lee et al. |
| 2005/0216079 A1 | 9/2005 | MaCoviak | | 2007/0213813 A1 | 9/2007 | Von Segesser et al. |
| 2005/0222674 A1 | 10/2005 | Paine | | 2007/0225801 A1 | 9/2007 | Drews et al. |
| 2005/0234545 A1 | 10/2005 | Nugent et al. | | 2007/0233237 A1 | 10/2007 | Krivoruchko |
| 2005/0234546 A1 | 10/2005 | Nugent et al. | | 2007/0239266 A1 | 10/2007 | Birdsall |
| 2005/0240259 A1 | 10/2005 | Sisken et al. | | 2007/0239269 A1 | 10/2007 | Dolan et al. |
| 2005/0240263 A1 | 10/2005 | Fogarty | | 2007/0239273 A1 | 10/2007 | Allen |
| 2005/0251252 A1 | 11/2005 | Stobie | | 2007/0255398 A1 | 11/2007 | Yang et al. |
| 2005/0261765 A1 | 11/2005 | Liddicoat | | 2007/0260305 A1 | 11/2007 | Drews et al. |
| 2005/0283231 A1 | 12/2005 | Haug et al. | | 2007/0265701 A1 | 11/2007 | Gurskis et al. |
| 2005/0384334 | 12/2005 | Haug et al. | | 2007/0270944 A1 | 11/2007 | Bergheim et al. |
| 2006/0004389 A1 | 1/2006 | Nguyen et al. | | 2007/0288089 A1 | 12/2007 | Gurskis et al. |
| 2006/0005129 A1 | 1/2006 | Wen et al. | | 2008/0004696 A1 | 1/2008 | Vesely |
| 2006/0025857 A1 | 2/2006 | Bergheim et al. | | 2008/0033543 A1 | 2/2008 | Gurskis et al. |
| 2006/0052867 A1 | 3/2006 | Revuelta et al. | | 2008/0071361 A1 | 3/2008 | Tuval et al. |
| 2006/0058871 A1 | 3/2006 | Zakay et al. | | 2008/0071369 A1 | 3/2008 | Tuval et al. |
| 2006/0058872 A1 | 3/2006 | Salahieh et al. | | 2008/0097595 A1 | 4/2008 | Gabbay |
| 2006/0074484 A1 | 4/2006 | Huber | | 2008/0119875 A1 | 5/2008 | Ino et al. |
| 2006/0085060 A1 | 4/2006 | Campbell | | 2008/0281411 A1 | 11/2008 | Berreklouw |
| 2006/0095125 A1 | 5/2006 | Chinn et al. | | 2008/0319543 A1 | 12/2008 | Lane |
| 2006/0122634 A1 | 6/2006 | Ino | | 2009/0036903 A1 | 2/2009 | Ino et al. |
| 2006/0122692 A1 | 6/2006 | Gilad et al. | | 2009/0112233 A1 | 4/2009 | Xiao |
| 2006/0135964 A1 | 6/2006 | Vesely | | 2009/0192599 A1 | 7/2009 | Lane et al. |
| 2006/0136052 A1 | 6/2006 | Vesely | | 2009/0192602 A1 | 7/2009 | Kuehn |
| 2006/0136054 A1 | 6/2006 | Berg et al. | | 2009/0192603 A1 | 7/2009 | Ryan |
| 2006/0149360 A1 | 7/2006 | Schwammenthal et al. | | 2009/0192604 A1 | 7/2009 | Gloss |
| 2006/0149367 A1 | 7/2006 | Sieracki | | 2009/0192605 A1 | 7/2009 | Gloss et al. |
| 2006/0154230 A1 | 7/2006 | Cunanan | | 2009/0192606 A1 | 7/2009 | Gloss et al. |
| 2006/0161249 A1 | 7/2006 | Realyvasquez et al. | | 2009/0210052 A1 | 8/2009 | Powell et al. |
| 2006/0167543 A1 | 7/2006 | Bailey et al. | | 2009/0264903 A1 | 10/2009 | Lee et al. |
| 2006/0173537 A1 | 8/2006 | Yang et al. | | 2009/0319038 A1 | 12/2009 | Gurskis et al. |
| 2006/0195183 A1 | 8/2006 | Navia et al. | | 2010/0030244 A1 | 2/2010 | Woolfson et al. |
| 2006/0195184 A1 | 8/2006 | Lane | | 2010/0044410 A1 | 2/2010 | Argentine et al. |
| 2006/0195185 A1 | 8/2006 | Lane | | 2010/0100174 A1 | 4/2010 | Gurskis |
| 2006/0195186 A1 | 8/2006 | Drews | | 2010/0249894 A1 | 9/2010 | Oba et al. |
| 2006/0207031 A1 | 9/2006 | Cunanan et al. | | | | |
| 2006/0229708 A1 | 10/2006 | Powell et al. | | FOREIGN PATENT DOCUMENTS | | |
| 2006/0235508 A1 | 10/2006 | Lane | | DE | 19532973 | 11/1996 |
| 2006/0241745 A1 | 10/2006 | Solem | | EP | 0 084 395 | 8/1986 |
| 2006/0246888 A1 | 11/2006 | Bender et al. | | EP | 0 096 721 | 12/1987 |
| 2006/0253191 A1 | 11/2006 | Salahieh et al. | | EP | 0 125 393 | 12/1987 |
| 2006/0259134 A1 | 11/2006 | Schwammenthal et al. | | EP | 0 179 562 | 7/1989 |
| 2006/0259135 A1 | 11/2006 | Navia et al. | | EP | 0 826 340 | 3/1998 |
| 2006/0259136 A1 | 11/2006 | Nguyen et al. | | EP | 0 850 607 | 7/1998 |
| 2006/0265056 A1 | 11/2006 | Nguyen et al. | | EP | 1057460 | 12/2000 |
| 2006/0271172 A1 | 11/2006 | Tehrani | | EP | 1 088 529 | 4/2001 |
| 2006/0271175 A1 | 11/2006 | Woolfson et al. | | EP | 1171059 | 1/2002 |
| 2006/0276888 A1 | 12/2006 | Lee | | EP | 971 650 | 1/2005 |
| 2006/0287717 A1 | 12/2006 | Rowe et al. | | EP | 171 059 | 2/2005 |
| 2006/0287719 A1 | 12/2006 | Rowe et al. | | GB | 1093599 | 12/1967 |
| 2007/0010835 A1 | 1/2007 | Breton et al. | | GB | 1477643 | 6/1977 |
| 2007/0010876 A1 | 1/2007 | Salahieh et al. | | GB | 2011259 | 7/1979 |
| 2007/0010877 A1 | 1/2007 | Salahieh et al. | | GB | 2 056 023 | 3/1981 |
| 2007/0016285 A1 | 1/2007 | Lane | | GB | 2 069 843 | 9/1981 |
| 2007/0016286 A1 | 1/2007 | Herrmann et al. | | GB | 2254254 | 10/1992 |
| 2007/0016288 A1 | 1/2007 | Gurskis | | GB | 2 279 134 | 12/1994 |
| 2007/0027461 A1 | 2/2007 | Gardiner et al. | | SU | 1116573 | 7/1985 |
| 2007/0035361 A1 | 2/2007 | Houser et al. | | WO | WO 87/05489 A1 | 9/1987 |
| 2007/0043435 A1 | 2/2007 | Seguin et al. | | WO | 89/00084 | 2/1989 |
| 2007/0078509 A1 | 4/2007 | Lotfy | | WO | 91/15167 | 10/1991 |
| 2007/0078510 A1 | 4/2007 | Ryan | | WO | 92/01269 | 8/1992 |
| 2007/0095698 A1 | 5/2007 | Cambron | | WO | 92/13502 | 8/1992 |
| 2007/0100440 A1 | 5/2007 | Figulla et al. | | WO | 92/19184 | 11/1992 |
| 2007/0106313 A1 | 5/2007 | Golden et al. | | WO | 92/19185 | 11/1992 |
| 2007/0129794 A1 | 6/2007 | Realyvasquez | | WO | 95/17139 | 6/1995 |
| 2007/0129795 A1 * | 6/2007 | Hill et al. .......... 623/2.11 | | WO | 95/28899 | 11/1995 |

| | | |
|---|---|---|
| WO | 96/40006 | 12/1996 |
| WO | 97/09933 | 3/1997 |
| WO | 97/09944 | 3/1997 |
| WO | 97/27799 | 8/1997 |
| WO | 97/41801 | 11/1997 |
| WO | 97/42871 | 11/1997 |
| WO | 98/06329 | 2/1998 |
| WO | 99/11201 | 3/1999 |
| WO | WO 99/15112 A1 | 4/1999 |
| WO | 99/51169 | 10/1999 |
| WO | 00/32105 | 6/2000 |
| WO | 00/40176 | 7/2000 |
| WO | 00/44311 | 8/2000 |
| WO | 00/47139 | 8/2000 |
| WO | WO 00/47139 A1 * | 8/2000 |
| WO | WO 00/56250 | 9/2000 |
| WO | WO 00/56250 A1 | 9/2000 |
| WO | 00/60995 | 10/2000 |
| WO | WO 00/59382 A1 | 10/2000 |
| WO | WO 00/64380 A1 | 11/2000 |
| WO | 01/10310 | 2/2001 |
| WO | 01/10312 | 2/2001 |
| WO | 01/49217 | 7/2001 |
| WO | 01/58363 | 8/2001 |
| WO | WO 01/76510 A2 | 10/2001 |
| WO | WO 01/76510 A3 | 10/2001 |
| WO | 01/82840 | 11/2001 |
| WO | 01/87190 | 11/2001 |
| WO | 03/011195 | 2/2003 |
| WO | 03/063740 | 8/2003 |
| WO | 04/006810 | 1/2004 |
| WO | 04/089246 | 10/2004 |
| WO | 05/004753 | 1/2005 |
| WO | 05/020842 | 3/2005 |
| WO | 05/039452 | 5/2005 |
| WO | 05/072655 | 8/2005 |
| WO | 06/086135 | 8/2006 |
| WO | 09/137517 | 11/2009 |

OTHER PUBLICATIONS

Lutter, et al., Percutaneous Valve Replacement: Current State and Future Prospects; Ann. Thorac. Surg. 2004;78:2199-2206.

Jansen, et al., "Detachable Shape-Memory Sewing Ring for Heart Valves," Artif. Organs. vol. 16, No. 3, 1992, pp. 294-297, Helmholtz Institute for Biomedical Engineering, Technical University of Aachen, Aachn, Germany,.

Tascon, "Prosthetic Heart Valves: Design Considerations," Ann. Thorac. Surgery, 48:S16-S17 (1989).

* cited by examiner

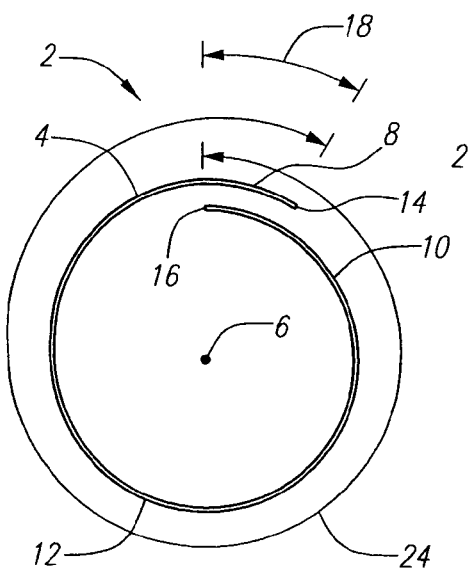
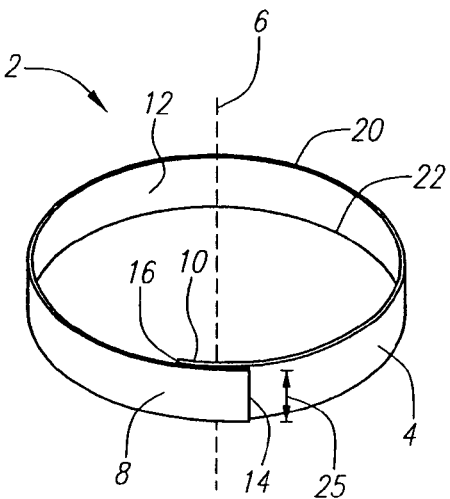
FIG. 1
FIG. 2
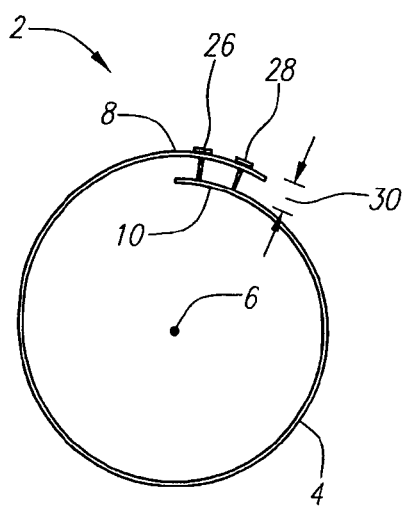
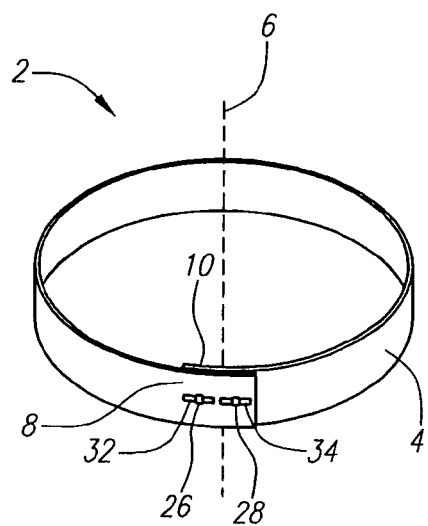
FIG. 3
FIG. 4

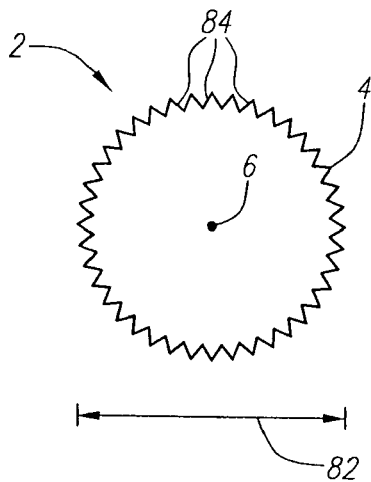
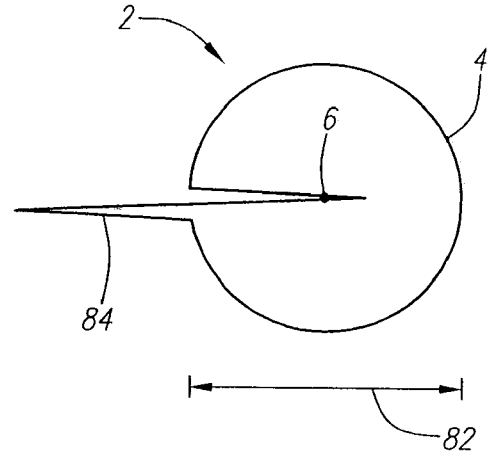
FIG. 17                    FIG. 18
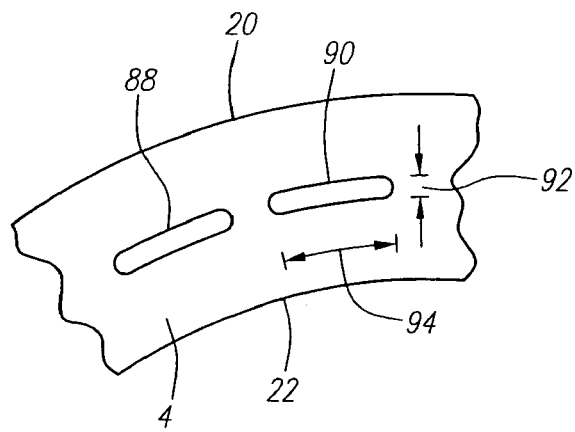
FIG. 20
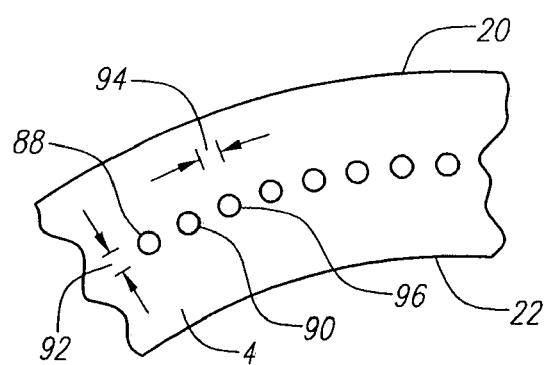
FIG. 21

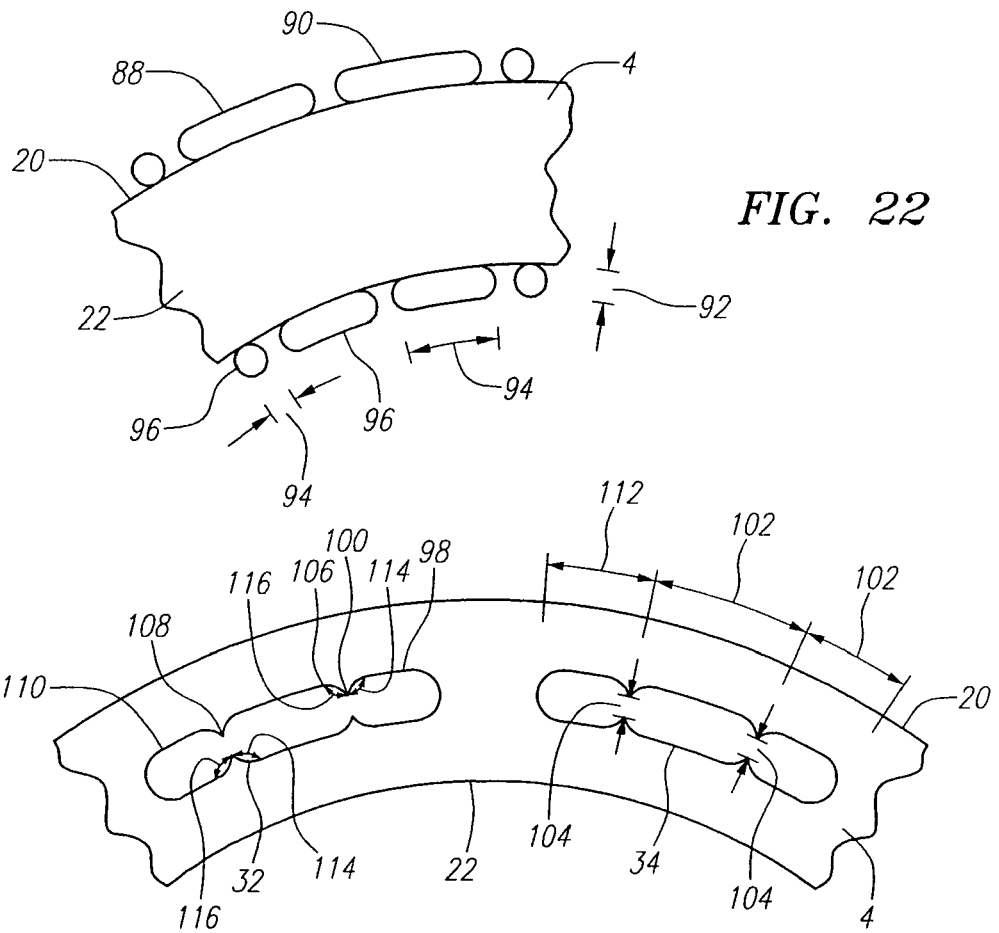
FIG. 22
FIG. 23
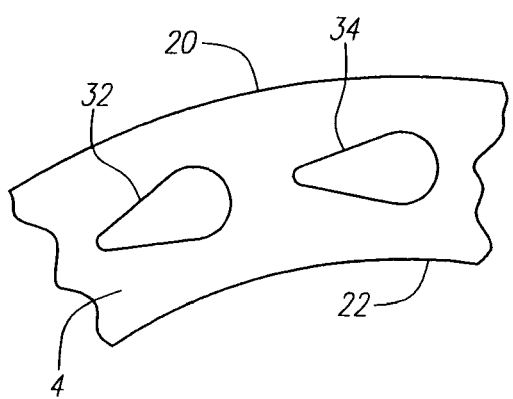
FIG. 24
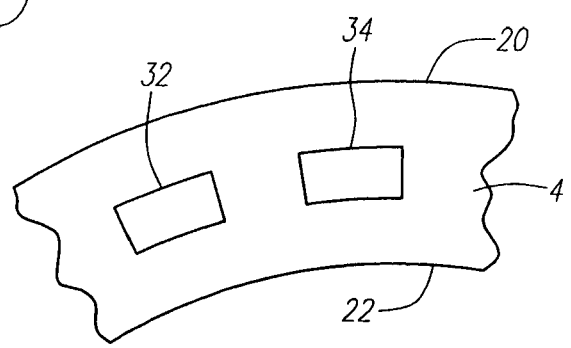
FIG. 25

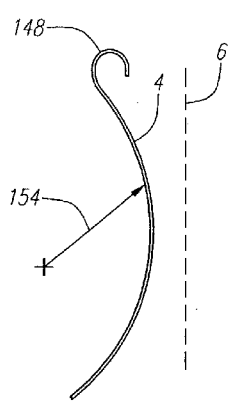
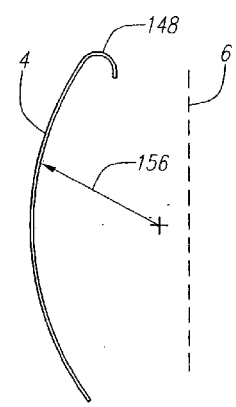
FIG. 39  FIG. 40
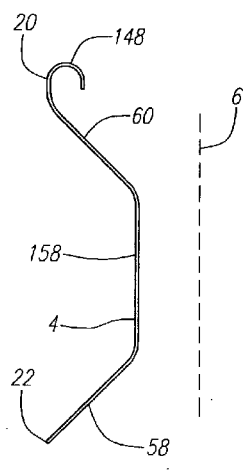
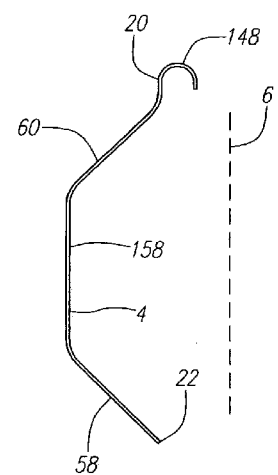
FIG. 41  FIG. 42

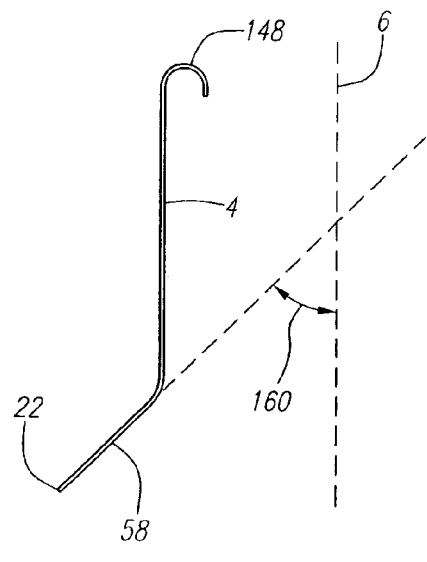
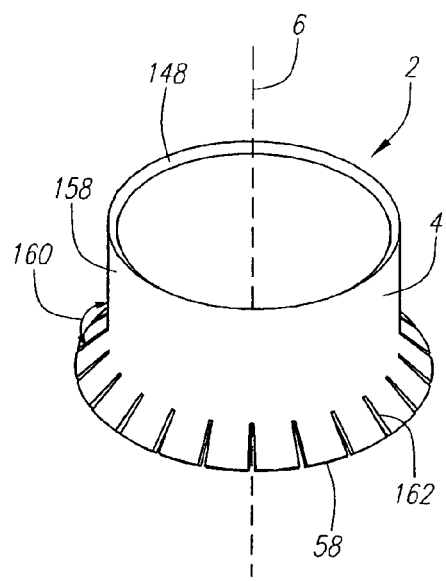
FIG. 43
FIG. 44
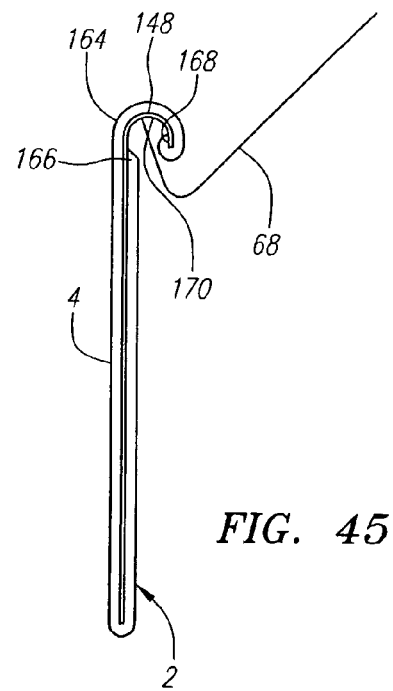
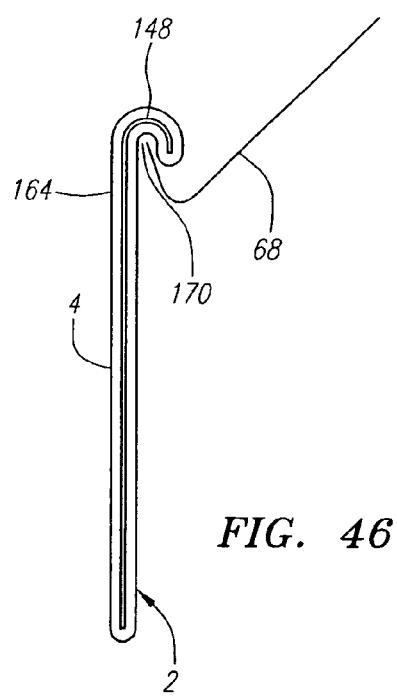
FIG. 45
FIG. 46

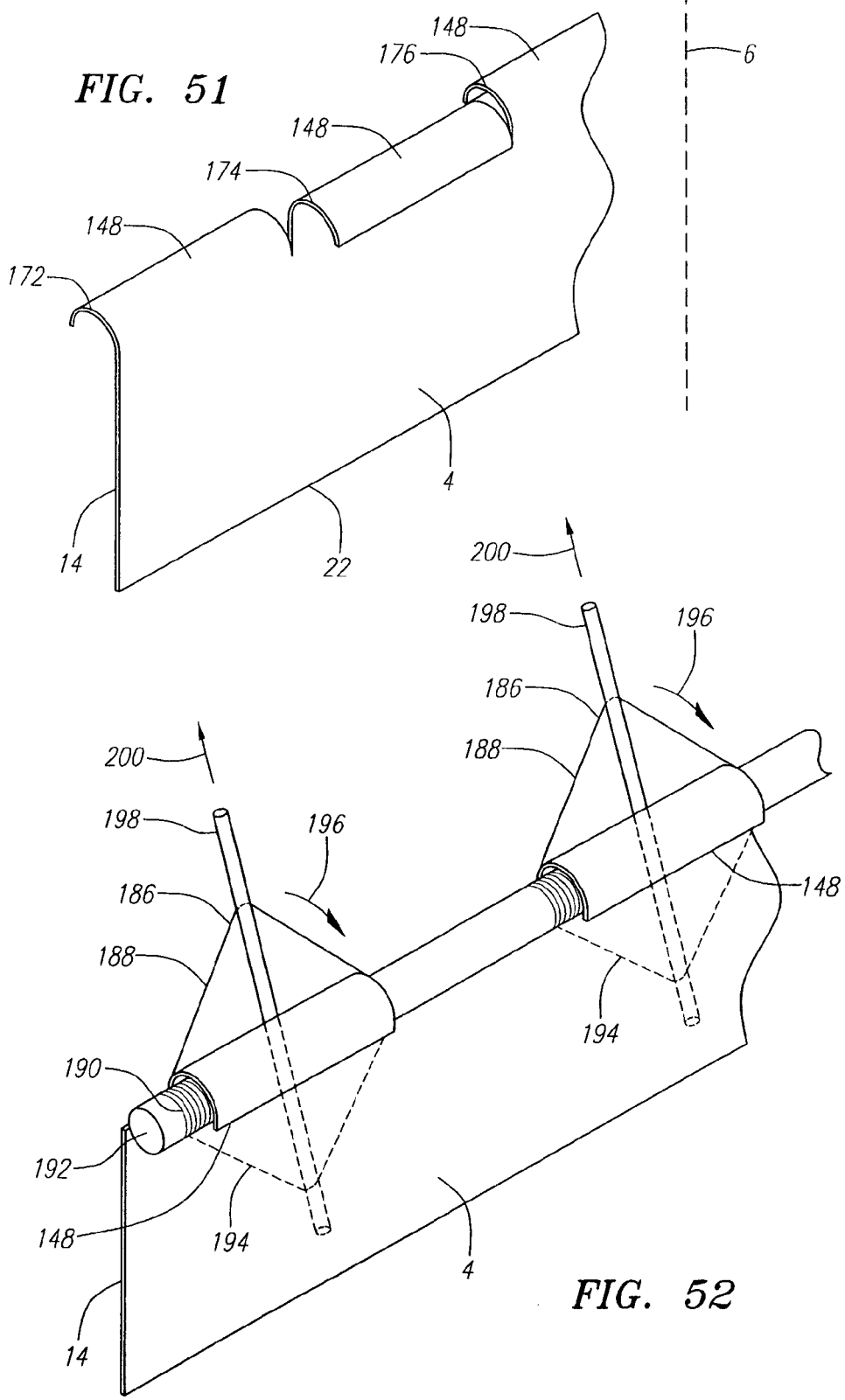

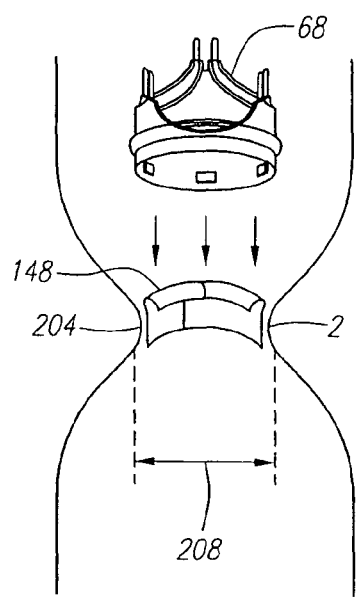
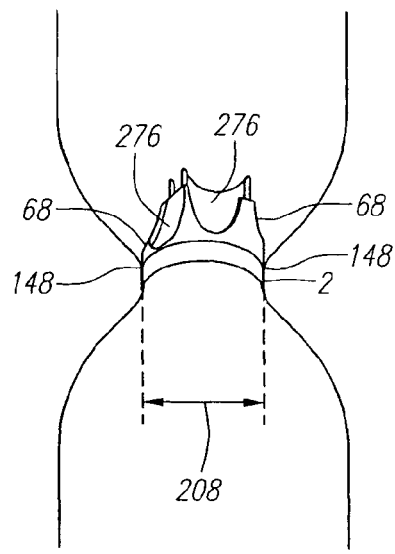
FIG. 69
FIG. 70
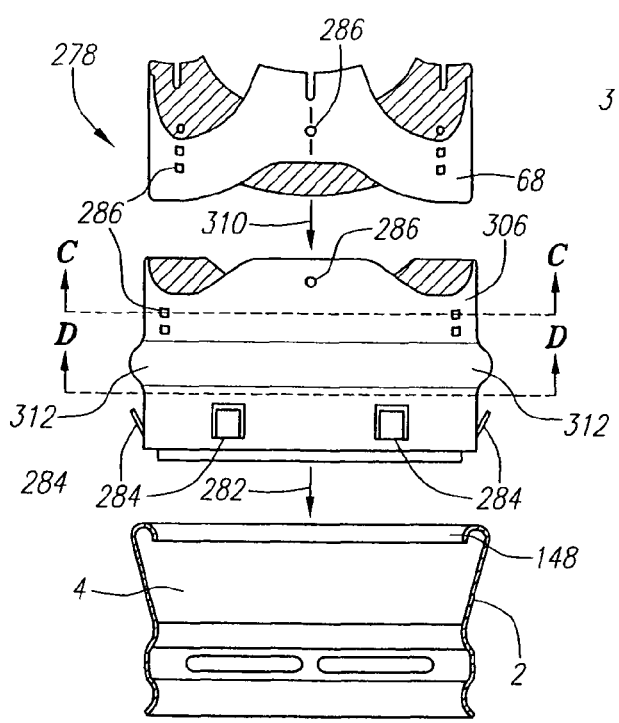
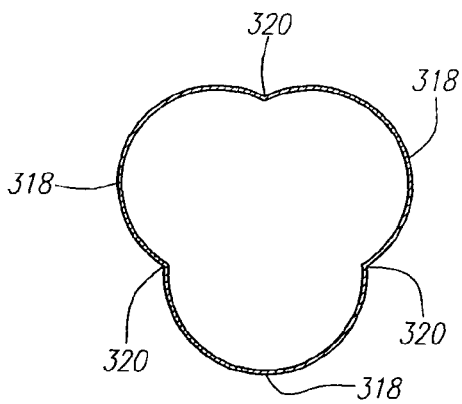
FIG. 79
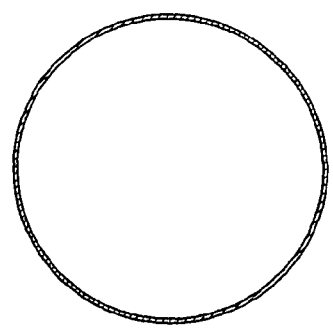
FIG. 78
FIG. 80

BIOLOGICALLY IMPLANTABLE HEART VALVE SYSTEM

CROSS-REFERENCE TO RELATED APPLICATIONS

This is a continuation of application Ser. No. 10/327,821, filed Dec. 20, 2002.

BACKGROUND OF THE INVENTION

1. Field of the Invention

The present invention relates generally to a biologically implantable prosthesis, a heart valve assembly using the prosthesis, and methods of using the same within an annulus of the body.

2. Description of the Related Art

Prosthetic heart valves can replace defective human valves in patients. Prosthetic valves commonly include sewing rings or suture cuffs that are attached to and extend around the outer circumference of the prosthetic valve orifice.

In a typical prosthetic valve implantation procedure, the heart is incised and the defective valve is removed leaving a surrounding area of locally tougher tissue. Known heart valve replacement techniques include individually passing sutures through the tough tissue to form an array of sutures. Free ends of the sutures are extended out of the thoracic cavity and laid, spaced apart, on the patient's body. The free ends of the sutures are then individually threaded through an edge around the circumference of the sewing ring. Once all sutures have been run through the ring, all the sutures are pulled up taught and the prosthetic valve is slid or "parachuted" down into place adjacent the tough tissue. Thereafter, the prosthetic valve is secured in place by traditional knot tying with the sutures.

The sewing ring is often made of a biocompatible fabric through which a needle and suture can pass. The prosthetic valves are typically sutured to a biological mass or annulus that is left when the surgeon removes the existing valve from the patient's heart. The sutures are tied snugly, thereby securing the sewing ring to the annulus and, in turn, the prosthetic valve to the heart.

Sewing rings can be tedious to secure to the valve orifice. Further, attaching the sewing ring to the annulus can be time consuming and cumbersome. The complexity of suturing provides a greater opportunity for mistakes and requires a patient to be on cardiopulmonary bypass for a lengthy period. It is also desirable to provide as large of a lumen through the prosthetic valve as possible to improve hemodynamics. However, techniques for attaching the sewing ring to the orifice typically require the area of the valve lumen be reduced to accommodate an attachment mechanism. For example, the sewing ring is typically retained on top of the annulus, resulting in a lumen that is, at the largest, the size of the original lumen.

A patient can also have a natural valve lumen that is detrimentally small. In these cases, the natural valve can be gusseted before the prosthetic valve is implanted. To gusset the natural valve, a longitudinal incision can be made along the wall of the lumen. The lumen can then be circumferentially expanded and the now-expanded incision can be covered with a patch graft or other membrane and stitched closed.

U.S. Pat. No. 4,743,253 to Magladry discloses a suture ring with a continuous compression ring. Magladry's ring is ductile, but provides a compressive, not expansive, force. In fact, the ring taught by Magladry is intended for placement over a heart valve and provides compression on the heart valve.

U.S. Pat. No. 6,217,610 to Carpentier et al. discloses an expandable annuloplasty ring. Carpentier et al. teach expanding the ring over the life of a patient by increasing the size of the ring by balloon dilatation. The ring is intended to remodel the shape of the valve annulus, not serve as a foundation to attach a second prosthesis and form a heart valve.

U.S. Pat. No. 5,984,959 to Robertson et al. discloses an expandable heart valve ring for attaching a synthetic valve thereto and a tool for attaching the ring to the synthetic valve. Robertson et al. teach the ring as having tabs that are used to attach to the second prosthesis by using a second device to engage the tabs.

There is a need for a circumferentially expandable bioprosthesis. There is also a need for a prosthesis and method that can expand an annulus and maintain an enlarged annulus circumference. Furthermore, there is a need for a minimally invasive heart valve replacement procedure. Also, there is a need for a prosthesis that can provide for the above and engagement with a second prosthesis, for example, the crown of a heart valve. Furthermore, there is a need for the above prosthesis that can self-engage a second prosthesis to improve implantation time.

BRIEF SUMMARY OF THE INVENTION

One embodiment of the disclosed prosthesis is a biologically implantable first prosthesis for a heart valve having a circumferentially expandable wall. The wall has a latitudinal cross-section perpendicular to the longitudinal axis, and a longitudinal cross-section parallel to the longitudinal axis. The prosthesis also has an engagement element configured to self-engage a second prosthesis.

The first prosthesis can also have a stop, where the stop prevents the wall from circumferentially decreasing. The first prosthesis can also have a fixturing device connector. The wall can also be corrugated. The wall can also have a turned lip on its leading edge. The first prosthesis can also be in an assembly where the first prosthesis can receive a second prosthesis, for example a crown.

Another embodiment of the prosthesis is a biologically implantable first prosthesis for a heart valve having a wall with a first edge and a second edge. The wall has a longitudinal axis at the center of the first prosthesis, and the first edge has an engagement element for engaging a second prosthesis. The engagement element is also turned toward the second edge.

The engagement element can be curved toward the second edge. The first edge can be the leading edge. The first prosthesis can also have a fixturing device connector that can be a port in the wall. The wall can also be corrugated. The first prosthesis can also be in an assembly with a second prosthesis connected to the engagement element. The second prosthesis can be a crown.

An embodiment of a method of implanting a heart valve in a valve annulus is attaching a first prosthesis to the valve annulus and attaching a second prosthesis to the first prosthesis. The first prosthesis has a circumferentially expandable wall. The wall has a longitudinal axis, and the wall has a latitudinal cross-section perpendicular to the longitudinal axis.

The first prosthesis can be a ring. The second prosthesis can be a crown. The wall of the first prosthesis can have a first terminal end and a second terminal end. Attaching the first prosthesis can include fixing the first prosthesis to a biological mass with a fixturing device. Attaching the first prosthesis can also include snap-fitting the second prosthesis to the first prosthesis.

Another embodiment of a method of implanting a heart valve in a valve annulus includes attaching a first prosthesis to the valve annulus and attaching a second prosthesis to the first prosthesis. The first prosthesis has a wall having a first edge and a second edge. The wall also has a longitudinal axis. The first edge comprises an engagement element, and the engagement element is turned toward the second edge.

The engagement element can be turned away from the longitudinal axis. The first prosthesis can be a ring. The second prosthesis can be a crown. Attaching the crown can include snap-fitting the crown to the first prosthesis.

An embodiment of a method of increasing and maintaining the size of a biological valve annulus includes placing a circumferentially expandable first prosthesis in the annulus. The method also includes circumferentially expanding the first prosthesis, and circumferentially locking the first prosthesis.

Circumferentially expanding the first prosthesis can include increasing the radius of the annulus from about 0.1 mm (0.004 in.) to more than about 2.0 mm (0.08 in.). The first prosthesis can also have an engagement element configured to receive a second prosthesis.

BRIEF DESCRIPTION OF THE DRAWINGS

FIG. 1 is a bottom view of an embodiment of the prosthesis.
FIG. 2 is a top perspective view of the embodiment of the prosthesis of FIG. 1.
FIG. 3 is a bottom view of another embodiment of the prosthesis.
FIG. 4 is a top perspective view of the embodiment of the prosthesis of FIG. 3.
FIGS. 16-18 are top views of various deformable embodiments of the prosthesis in unexpanded states.
FIGS. 20-22 illustrate various embodiments of the fixturing device connectors.
FIGS. 23-25 illustrate various embodiments of the receiving elements.
FIGS. 35-43 are cross-sections of various embodiments of the wall of the prosthesis.
FIG. 44 illustrates an embodiment of the prosthesis of FIG. 38.
FIGS. 45 and 46 illustrate cross-sections of the wall of the prosthesis with various embodiments of the covering.
FIGS. 47-52 illustrate various embodiments of the engagement element.
FIG. 69 is a cut-away view of positioning the second prosthesis onto the first prosthesis with a solid view of the second prosthesis.
FIG. 70 is a cut-away view of attaching the second prosthesis to the first prosthesis.
FIG. 78 is an exploded view of an embodiment of attaching the second prosthesis to an adapter and attaching the adapter to the first prosthesis.
FIGS. 79 and 80 illustrate cross-sections C-C and D-D, respectively, from FIG. 78.

DETAILED DESCRIPTION

Figure 5:
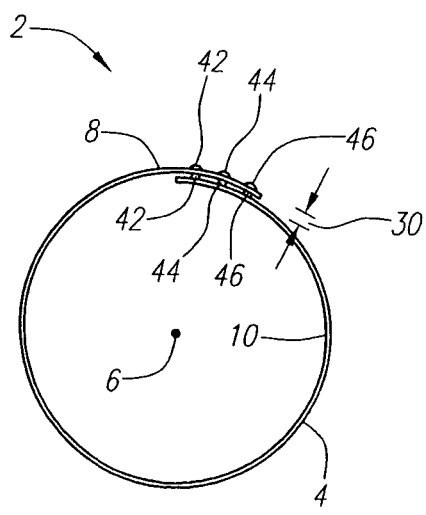
FIG. 5 is a bottom view of another embodiment of the prosthesis.

FIGS. 1 and 2 illustrate an embodiment of a biologically implantable first prosthesis 2. The first prosthesis 2 can have a wall 4. The wall 4 can have material strength and dimensions known to one having ordinary skill in the art to make the first prosthesis resiliently expandable. The wall 4 can have an open form or spiral longitudinal cross-section, as shown in FIG. 1. The longitudinal cross-section can be perpendicular to a central longitudinal axis 6.

The wall 4 can have a first terminal end 8 and a second terminal end 10. Each end 8 and 10 can be defined from a midpoint 12 of the wall 4 to a first terminus 14 or a second terminus 16 of the wall 4 at the respective end 8 or 10. The wall 4 can have an end difference length 18. The end difference length 18 can be the shortest angular length from the first terminus 14 to the second terminus 16. The wall 4 can also have a leading edge 20 and a trailing edge 22. The leading edge 20 and trailing edge 22 can be substantially perpendicular to the longitudinal axis 6. The first prosthesis 2 can have a circumference equivalent to a wall length 24 minus an end difference length 18. The wall 4 can have a wall height 25. The wall height can be from about 3.18 mm (0.125 in.) to about 12.7 mm (0.500 in.), for example about 8.26 mm (0.325 in.). The wall 4 can also be void of any attachment device with which to fix one end 8 or 10 of the wall 4 to the other end 8 or 10 of the wall 4. The wall 4 can made from stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), polymers such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, silicone, radiopaque materials or combinations thereof. Examples of radiopaque materials are barium, sulfate, titanium, stainless steel, nickel-titanium alloys and gold.

FIGS. 3 and 4 illustrate an embodiment of the first prosthesis 2 that can be mechanically expandable. A first protrusion 26 and a second protrusion 28 at the first terminal end 8 can extend from the wall 4. The protrusions 26 and 28 can extend perpendicular to the wall 4 or perpendicular to the longitudinal axis 6. The protrusions 26 and 28 can be tabs, brads, extensions, balls, rods or a combination thereof. The protrusions can have a protrusion depth 30 sufficient to retain the wall 4.

The wall 4 can also have a first receiving element 32 and a second receiving element 34 at the second terminal end 10 that receive or engage the first protrusion 26 and the second protrusion 28, respectively. The wall 4 can also have more or less (e.g., one or zero) receiving elements 32 or 34. The receiving elements 32 and 34 can be holes in the wall 4. The receiving elements 32 and 34 can also be divets, dimples, hooks, slots, or a combination thereof. The protrusions 26 and 28 and receiving elements 32 and 34 can act together as a stop, or an interference fit, to prevent the first prosthesis 2 from circumferentially extending or decreasing beyond desired limits.

Figure 6:
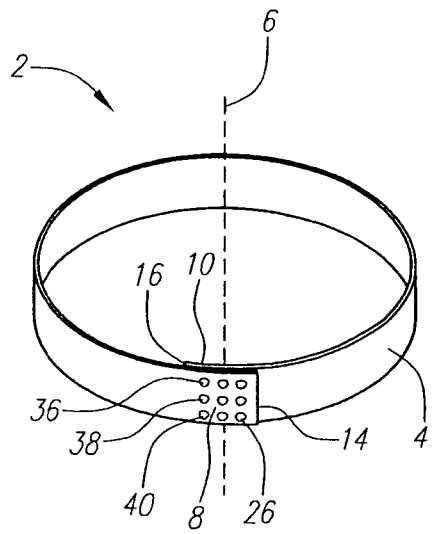
FIG. 6 is a top perspective view of the embodiment of the prosthesis of FIG. 5.

FIGS. 5 and 6 illustrate an embodiment of the first prosthesis 2 that can have protrusions 26 and receiving elements 32 that can be dimples. The protrusions 26 and receiving elements 32 can be in a first row 36, a second row 38, and additional rows 40. The protrusions 26 can also be in a first column 42, a second column 44, and additional columns 46. The receiving elements 32 can have a receiving element depth 46 within the same range of sizes as the protrusion depth 36, above.

Figure 7:
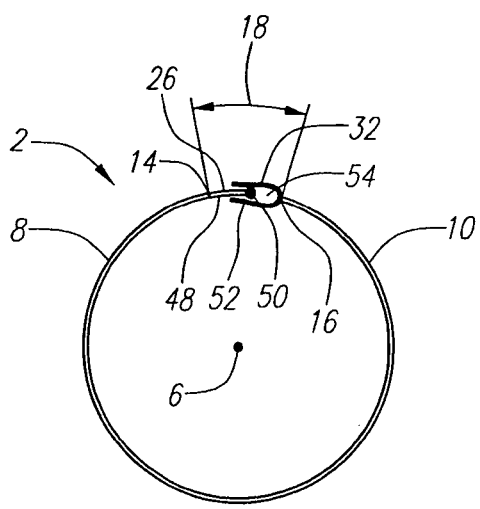
FIG. 7 is a bottom view of another embodiment of the prosthesis with cut-away views of the collars.
Figure 8:
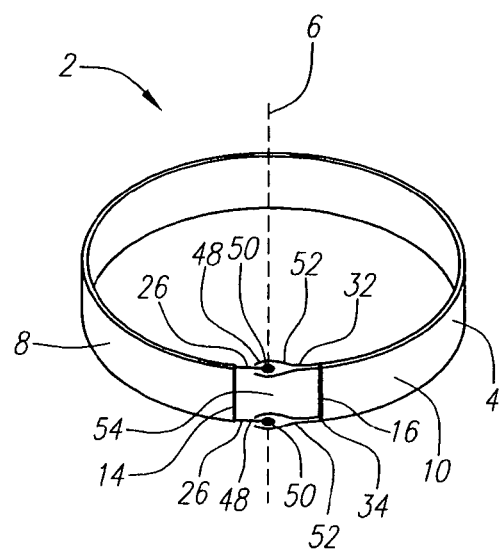
FIG. 8 is a top perspective view of the embodiment of the prosthesis of FIG. 7 with cut-away views of the collars.

FIGS. 7 and 8 illustrate an embodiment of the first prosthesis 2 that can have the protrusions 26 and 28 extending from the first terminus 14 substantially at a tangent to the wall 4. The protrusions 26 and 28 can be rods 48 with balls 50 at the ends of the rods 48. The receiving elements 32 and 34 can extend from the second terminus 16 substantially at a tangent to the wall 4. The receiving elements 32 and 34 can be collars 52 for receiving the balls 50. The wall 4 can have a longitudinal cross-section in the shape of a circular open curve, as shown in FIG. 7. A circumferential gap 54 can exist between the first terminus 14 and the second terminus 16.

Figure 9:
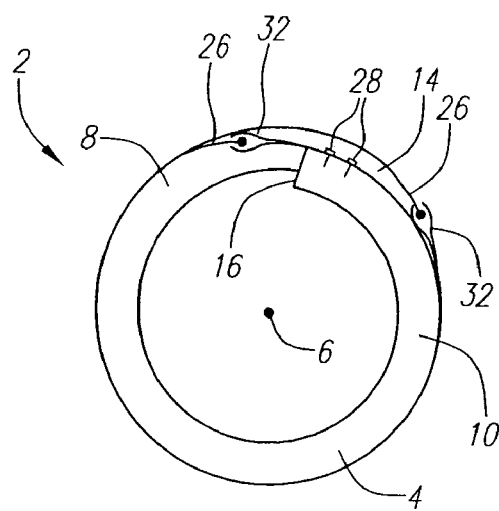
FIG. 9 is a bottom view of another embodiment of the prosthesis with cut-away views of the collars.
Figure 10:
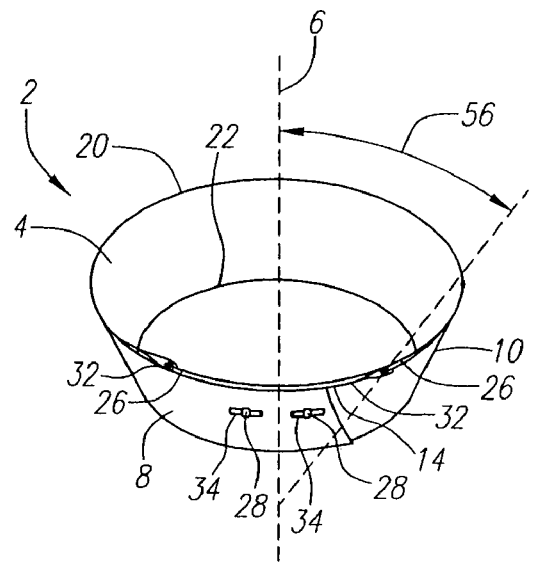
FIG. 10 is a top perspective view of the embodiment of the prosthesis of FIG. 8 with cut-away views of the collars.

FIGS. 9 and 10 illustrate an embodiment of the first prosthesis 2 that can have different embodiments of protrusions 26 and 28 and receiving elements 32 and 34. The first prosthesis 2 of FIGS. 9 and 10 can also have a wall angle 56 relative to the longitudinal axis 6 controlled by the dimensions of the protrusions 26 and 28 and receiving elements 32 and 34 and the locations of the protrusions 26 and 28 and receiving elements 32 and 34 on the wall 4. The wall angle 56 can be from about 10° to about 60°, more narrowly from about 20° to about 45°, for example about 25°. The protrusions 26 and 28 and the receiving elements 32 and 34 can be located along the trailing edge 22, the leading edge 20 or therebetween.

Figure 11:
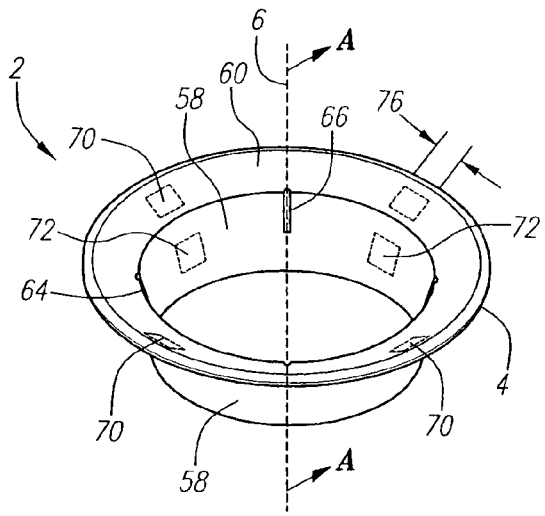
FIG. 11 is a top perspective view of another embodiment of the prosthesis with magnets.
Figure 12:
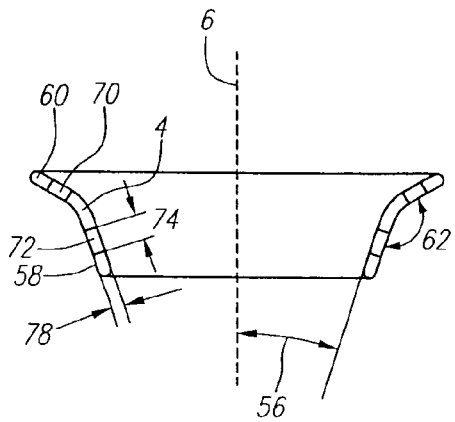
FIG. 12 illustrates cross-section A-A of FIG. 11.

FIGS. 11 and 12 illustrate an embodiment of the first prosthesis 2 with the wall 4 having a bottom segment 58 and a top segment 60. The first prosthesis 2 can be deformably circumferentially expandable. The bottom segment 58 can have the wall angle 56 relative to the longitudinal axis 6. The angle between the bottom segment 58 and the top segment 60 can be a joint angle 62. The joint angle 62 can be from about 90° to about 180°, more narrowly from about 90° to about 160°, for example about 120°. The wall 4 can also have a first steering groove 64 that can extend over the length of the bottom segment 58. The wall 4 can also have a second steering groove 66 that can extend over a portion of the length of the bottom segment 58. The grooves 64 and 66 can help angularly align, with respect to the longitudinal axis 6, a second prosthesis 68 that can be attached to the first prosthesis 2. The grooves 64 and 66 can also prevent the rotation of the first prosthesis 2 with respect to the second prosthesis 68. The second groove 66 can also help to longitudinally align the second prosthesis 68.

The first prosthesis 2 can also have engagement elements, for example top magnets 70 in the top segment 60 and bottom magnets 72 in the bottom segment 58. The magnets 70 and 72 can have a magnet height 74, a magnet width 76 and a magnet length 78. The magnets 70 and 72 can be rare earth, high strength-type magnets. The magnets can be made from neodymium-iron-boron and can be encapsulated in a coating made from PTFE (e.g., TEFLON® (from E. I. Du Pont de Nemours and Company, Wilmington, Del.), PEEK, a similarly inert and stable biocompatible polymer, or a combination thereof. A radiopaque material can also be added to the coating. The top and/or bottom magnets 70 and/or 72 can be customized to allow for only one angular orientation of the second prosthesis 68 by changing the polarity of one or an irregular number of magnets 70 and/or 72 (e.g., positive) to be different from the polarity of the remaining magnets 70 and/or 72 (e.g., negative).

In one example, 24 magnets 70 can be evenly distributed around the circumference of the first prosthesis 2. The magnet heights 74 can be about 3.175 mm (0.125 in.). The magnet widths 76 can be about 3.175 mm (0.125 in.). The magnet lengths 78 can be about 1.59 mm (0.0625 in.).

Figure 13:
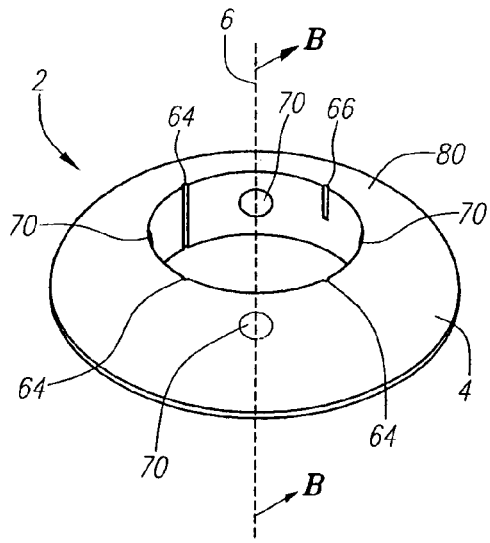
FIG. 13 is a top perspective view of another embodiment of the prosthesis with magnets.
Figure 14:
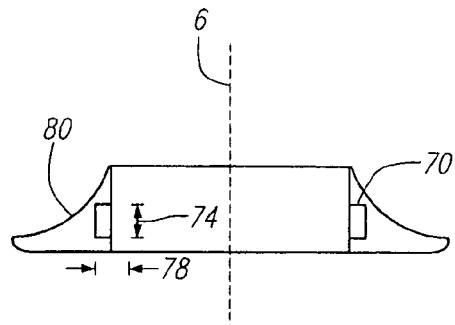
FIG. 14 illustrates cross-section B-B of FIG. 13.

FIGS. 13 and 14 illustrate an embodiment of the first prosthesis 2 similar to the embodiment illustrated in FIGS. 11 and 12. The present embodiment of the first prosthesis 2 can have a cloth sewing surface 80. The magnets 70 can be square or rectangular in cross-section (as shown in FIGS. 11 and 12) or oval or circular in cross-section (as shown in FIGS. 13 and 14). The wall 4 can also be multiple segments 58 and 60, as shown in FIGS. 11 and 12, or a single segment, as shown in FIGS. 13 and 14.

Figure 15:
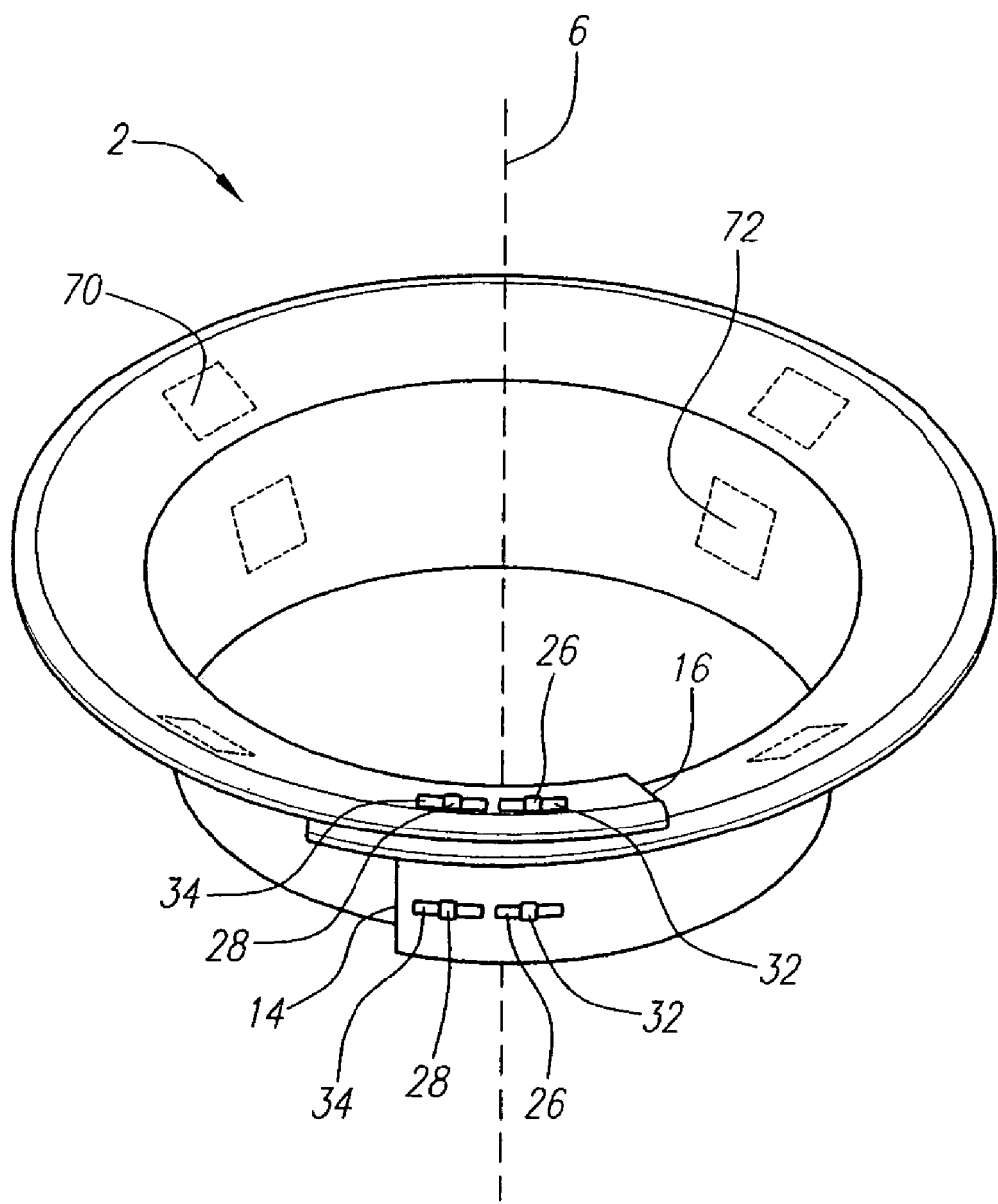
FIG. 15 is a top perspective view of another embodiment of the prosthesis with magnets.

FIG. 15 illustrates an embodiment of the first prosthesis 2 similar to the embodiment illustrates in FIGS. 11 and 12. The first prosthesis 2 in the present embodiment can also be mechanically and/or resiliently circumferentially expandable.

Figure 16:
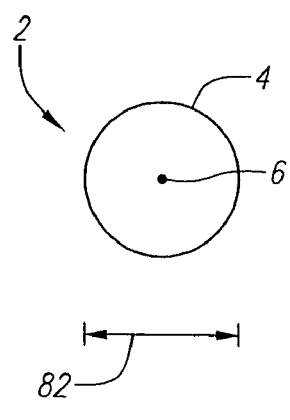
Figure 19:
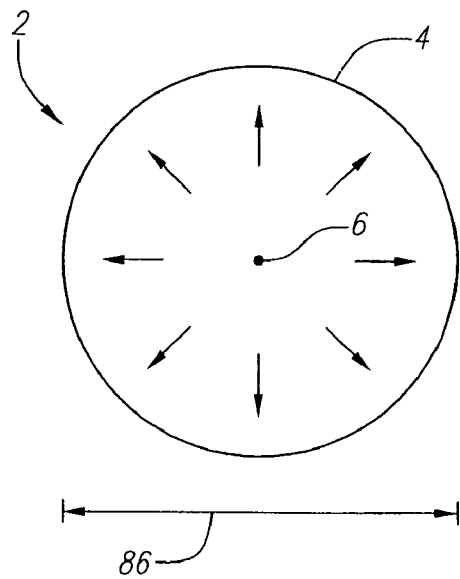
FIG. 19 is a top view of the embodiment of the prosthesis of FIG. 12 in an expanded state.

FIGS. 16-18 illustrate deformable embodiments of the first prosthesis 2. In an unexpanded state, the first prosthesis 2 can have an unexpanded diameter 82. The embodiment of the first prosthesis 2 in FIG. 16 can have a smooth wall 4, thereby relying on hoop strain to expand. In FIG. 17, the embodiment can have an accordianed wall 4 with multiple pleats or folds 84. The folds 84 can open or unfold to maximize circumferential expansion of the wall 4 during use. The embodiment of the first prosthesis 2 in FIG. 18 can have a single large fold 84 for the same purpose as the folds 84 shown in FIG. 17. FIG. 19 illustrates a deformable embodiment of the first prosthesis 2 in an expanded state. A radial force, as shown by arrows, directed away from the longitudinal axis 6 can expand the first prosthesis 2 to an expanded diameter 86. Materials and dimensions of the first prosthesis 2 can be selected by one having ordinary skill in the art to permit the ratio of the unexpanded diameter 82 to the expanded diameter 86 to be from about 0% to about 50%, more narrowly from about 5% to about 20%, yet more narrowly from about 9% to about 12%, for example about 9.5%.

FIG. 20 illustrates a length of the wall 4 that can have a first fixturing device connector 88 and a second fixturing device connector 90. The fixturing device connectors 88 and 90 can be ports or holes in the wall 4. The fixturing device connectors 88 and 90 can be ovular and can have a fixturing device connector height 92 and a fixturing device connector length 94. The fixturing device connector height 92 can be from about 0.51 mm (0.020 in.) to about 3.18 mm (0.125 in.), more narrowly from about 1.0 mm (0.040 in.) to about 1.5 mm (0.060 in.), for example about 1.3 mm (0.050 in).

FIG. 21 illustrates a length of the wall 4 that can have first, second, and additional fixturing device connectors 88, 90 and 96. The fixturing device connectors 88, 90 and 96 can be circular in shape. FIG. 22 illustrates a length of the wall 4 that can have the fixturing device connectors 88, 90 and 96 attached to the leading and trailing edges 20 and 22. The fixturing device connectors 88, 90 and 96 can be made from fabric or metal, for example polymers such as polyester (e.g., DACRON® from E. I. Du Pont de Nemours and Company, Wilmington, Del.), polypropylene, PTFE, ePTFE, nylon, extruded collagen, silicone, stainless steel alloys, nickel-titanium alloys (e.g., Nitinol), cobalt-chrome alloys (e.g., ELGILOY® from Elgin Specialty Metals, Elgin, Ill., CONICHROME® from Carpenter Metals Corp., Wyomissing, Pa.) or combinations thereof. Variously shaped and configured fixturing device connectors 88, 90 and 96 can be on the same wall 4.

FIG. 23 illustrates a length of the wall 4 that can have the receiving elements 32 and 34. The receiving elements 32 and 34 can be ports or holes in the wall 4. The receiving elements 32 and 34 and the fixturing device connectors 88, 90 and 96 can be the same element. The receiving elements 32 and 34 can have a first setting position 98 and a first neck 100 at one end of the first setting position 98. The first setting position 98 can have a setting position length 102 from about 4 mm (0.2 in.) to about 10 mm (0.4 in.), for example about 6.3 mm (0.25 in.). The first neck 100 can have a neck width 104. The first neck 100 can be at a first end of a second setting position 106. The receiving elements 32 and 34 can have more or less than two setting positions 98 and 106 (e.g., one or zero). At a second end of the second setting position 106, the second setting position 106 can have a second neck 108. The second neck 108 can be at a first end of a final stop position 110. The final stop position 110 can have a final stop length 112.

The first and second setting positions 98 and 106 can lead to the first and second necks 100 and 108, respectively, with a ramp angle 114. The stop position 110 and the second setting position 106 can lead to the second 108 and first necks 100, respectively, with a stop angle 116.

FIG. 24 illustrates narrowing oval or teardrop-shaped receiving elements 32 and 34. FIG. 25 illustrates rectangular receiving elements 32 and 34.

Figure 26:
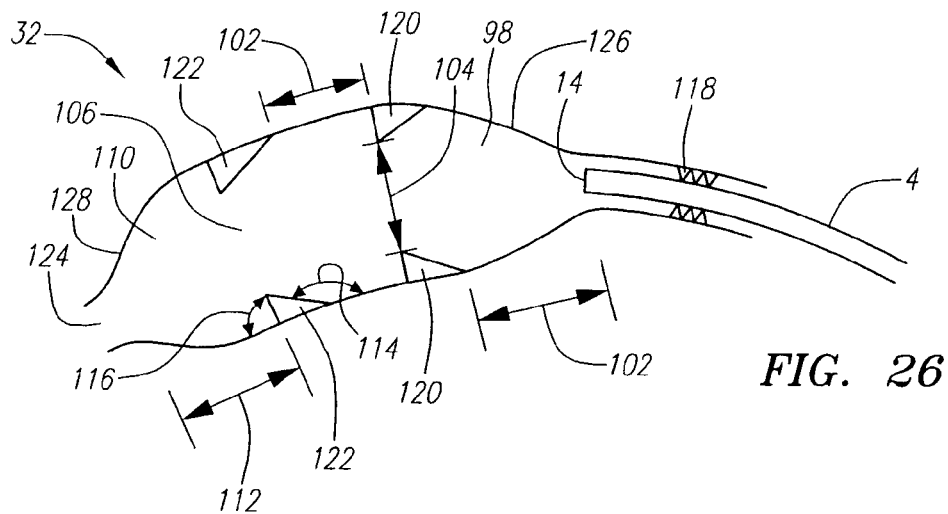
FIGS. 26 and 27 are cut-away views of various embodiments of the receiving elements.

FIG. 26 illustrates the receiving element 32 that can be in the shape of a collar or sleeve. The receiving element 32 can be attached by a connection zone 118 to a rod (not shown) extending from the wall 4 or to the wall 4 itself. The receiving element 32 can have first wedges 120 and second wedges 122. The length between the closest point of the first wedges 120 or of the second wedges 122 can be the neck width 104. The wedges 120 and 122 can revolve around the entire receiving element 32, thereby forming a single, circular first wedge 120 and a single, circular second wedge 122 (when seen in three-dimensions).

Figure 27:
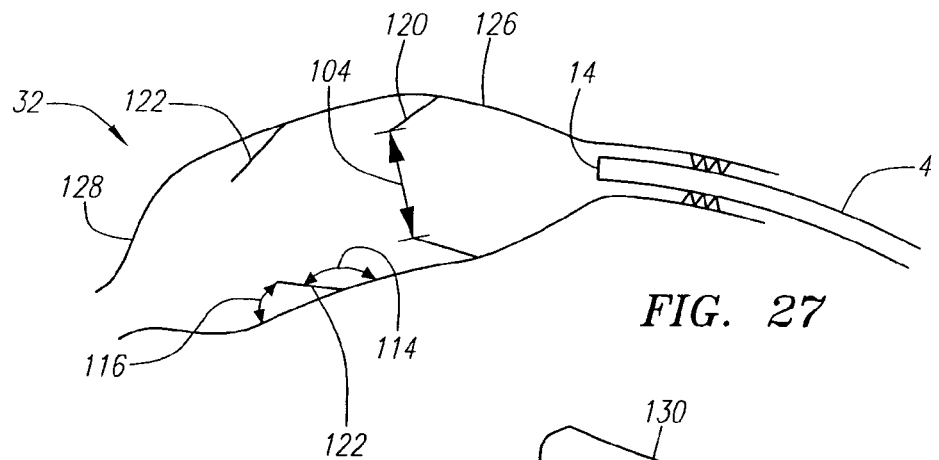

A receiving element shaftway 124 can be open at one end of the receiving element 32. The receiving element 32 can have a first narrowing 126 near the connection zone 118 and a second narrowing 128 near the receiving element shaftway 124. FIG. 27 illustrates the receiving element 32 that can have the wedges 120 and 122 shaped as scales or stop tabs.

Figure 28:
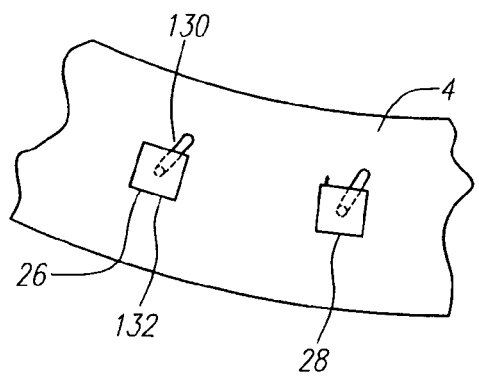
FIGS. 28-33 illustrate various embodiments of the protrusions.
Figure 29:
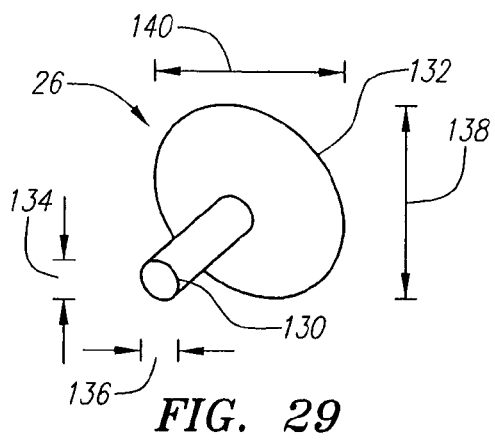
Figure 30:
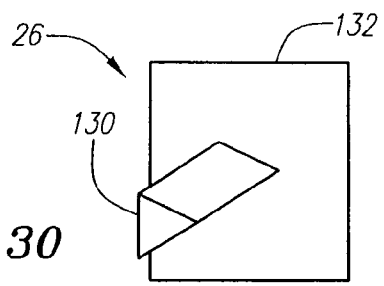

A length of the wall 4 that can have protrusions 26 and 28 is illustrated in FIG. 28. The protrusions 26 and 28, shown alone in various embodiments in FIGS. 29 and 25, can be made from an extension 130 and a cuff 132. The extension 130 can be shaped cylindrically or, as shown in FIG. 30, as a shaft with a triangular cross-section. The extension 130 can have an extension height 134 and an extension width 136. The extension height 134 can be from about 0.51 mm (0.020 in.) to about 2.54 mm (0.100 in.), for example about 1.3 mm (0.050 in.). The final stop length 112 can be from about the extension width 136 to about 10 mm (0.4 in.), for example about 6.3 mm (0.25 in.).

The cuff 132 can be shaped as a circle or a square and can be substantially flat in depth. The cuff 132 can have a cuff height 138 and a cuff width 140. The cuff height 138 can be from about the fixturing device connector height 92 to about 5.08 mm (0.200 in.), for example about 2.0 mm (0.080 in). The cuff width 140 can be within the range for the cuff height 138, above.

Figure 31:
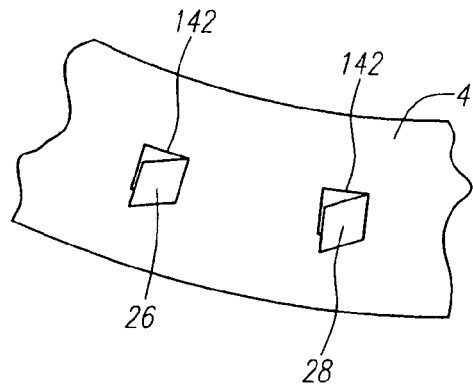

FIG. 31 illustrates a length of the wall 4 having the protrusions 26 and 28 formed from tabs cut out of the wall 4. Cut holes 142 can exist in the wall 4 where the material in the protrusions 26 and 28 was located in the wall 4 before being cut out.

Figure 32:
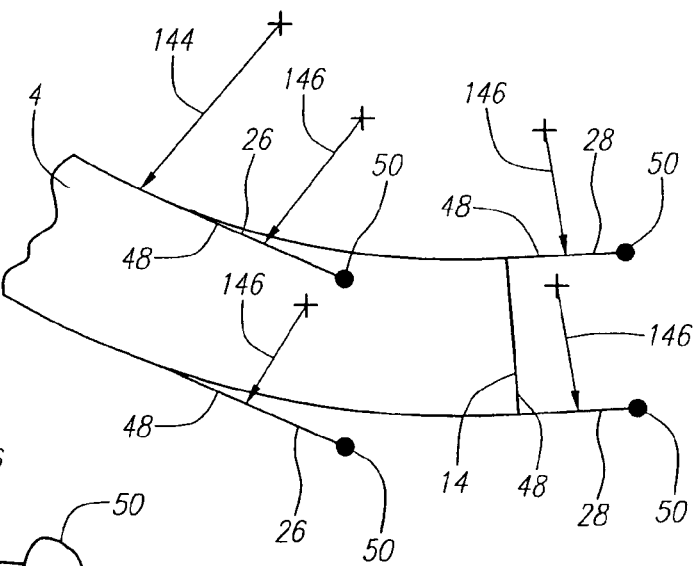

FIG. 32 illustrates a length of the wall 4 that can have a first set and a second set of protrusions 26 and 28 extending from the wall 4. The wall 4 can have a wall radius of curvature 144. The protrusions 26 and 28 can have protrusion radii of curvature 146. The protrusion radii of curvature 146 can be from about the wall radius of curvature 144 to infinity.

Figure 33:
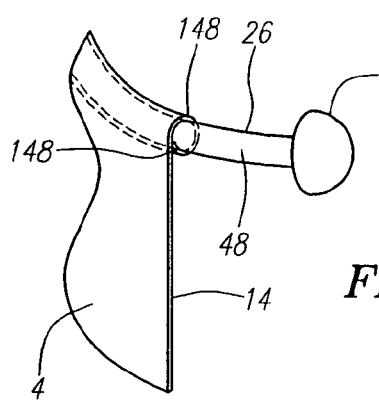

FIG. 33 illustrates a length of the wall 4 that can have an engagement element 148. The engagement element 148 can be shaped as a lip and wrapped around the protrusion 26. The engagement element 148 can enable the first prosthesis 2 to self-engage the second prosthesis 68. For example, the engagement element 148 can snap-fit to the second prosthesis 68.

Figure 34:
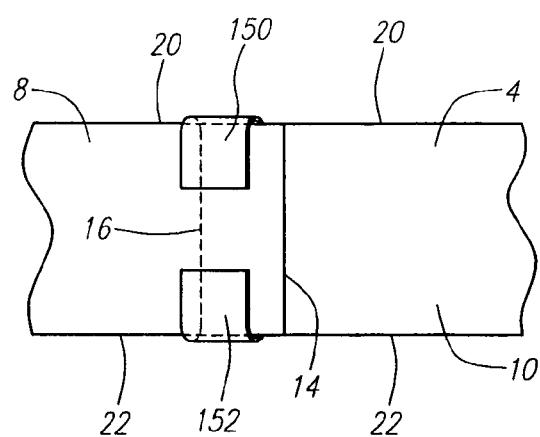
FIG. 34 illustrates the steering elements.

FIG. 34 illustrates the first terminal end 8 and the second terminal end 10. The second terminal end 10 can have a first guide 150 and a second guide 152 that can wrap around the leading edge 20 and the trailing edge 22, respectively, of the first terminal end 8. The first terminal end 8 can slide angularly, with respect to the longitudinal axis 6, within the guides 150 and 152. The guides 150 and 152 can also minimize the risk of the first terminal end 8 moving too far away from or becoming misaligned from the second terminal end 10.

Figure 35:
Figure 36:
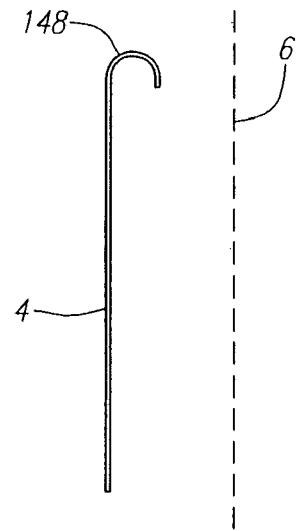

FIGS. 35-43 illustrate embodiments of the first prosthesis 2 at a latitudinal cross-section. The latitudinal cross-section can be a cross-section parallel with the longitudinal axis 6. FIG. 35 illustrates an embodiment with the wall 4 having a corrugated latitudinal cross-section. FIG. 36 illustrates an embodiment with the wall 4 having a straight latitudinal cross-section, parallel with the longitudinal axis 6.

Figure 37:
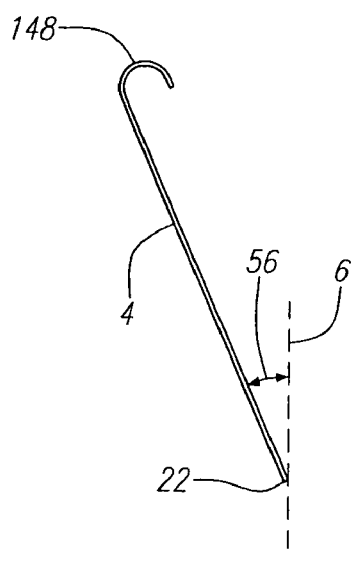
Figure 38:
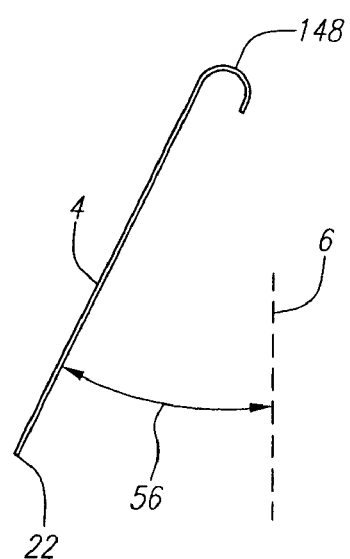

FIG. 37 illustrates an embodiment having the trailing edge 22 angled toward the longitudinal axis 6 at the wall angle 56. FIG. 38 illustrates an embodiment having the trailing edge 22 angled away from the longitudinal axis 6 at the wall angle 56.

FIG. 39 illustrates an embodiment having a wall 4 convex toward the longitudinal axis 6. The wall 4 can be straight or have a lateral convex radius of curvature 154. FIG. 40 illustrates an embodiment having a wall 4 concave toward the longitudinal axis 6. The wall 4 can have a lateral concave radius of curvature 156 within the same range as the lateral convex radius of curvature 154.

FIG. 41 illustrates an embodiment having a wall 4 with a top segment 60, a middle segment 158 and a bottom segment 58. The top segment 60 and leading edge 20 can be angled away from the longitudinal axis 6. The bottom segment 58 and trailing edge 22 can be angled away from the longitudinal axis 6. The middle segment 158 can remain parallel to the longitudinal axis 6.

FIG. 42 illustrates an embodiment having the top segment 60 and the leading edge 20 that can be angled toward the longitudinal axis 6. The bottom segment 58 and trailing edge 22 can also be angled toward the longitudinal axis 6. The middle segment 158 can remain parallel to the longitudinal axis 6.

FIGS. 43 and 44 illustrate an embodiment of the wall 4 that can have a bottom segment 58 that can extend from the wall 4 at a retainer angle 160 with respect to the longitudinal axis 6 from about 0° to about 90°, more narrowly from about 10° to about 50°, for example about 30°. The bottom segment 58 can also have cuts 162, shown in FIG. 44. The cuts 162 can minimize stresses when the bottom segment 58 fans away from the middle segment 158. The bottom segment 58 can also act as a retention element, extending beyond the typical trailing edge 22 and stabilizing the first prosthesis 2 after the first prosthesis 2 is implanted.

FIG. 45 illustrates a cross-section of the wall 4 that can have a fabric covering 164, for example polyester (e.g., DACRON® from E. I. du Pont de Nemours and Company, Wilmington, Del.), polypropylene, PTFE, ePTFE, nylon, extruded collagen, silicone or combinations thereof. The fabric can be attached to the wall 4 at a first attachment point 166 and a second attachment point 168. The bare area of the wall between the attachment points 166 and 168 can be the engagement surface 170. The second prosthesis 68 can engage the first prosthesis 2 at the engagement surface 170.

FIG. 46 illustrates a cross-section of the wall 4 covered entirely by the covering 164. The second prosthesis 68 can also engage the first prosthesis 2 at the engagement surface 170 covered by the covering 164.

Figure 47:
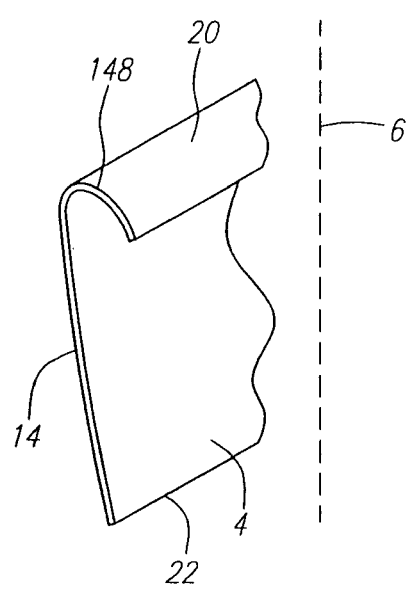
Figure 48:
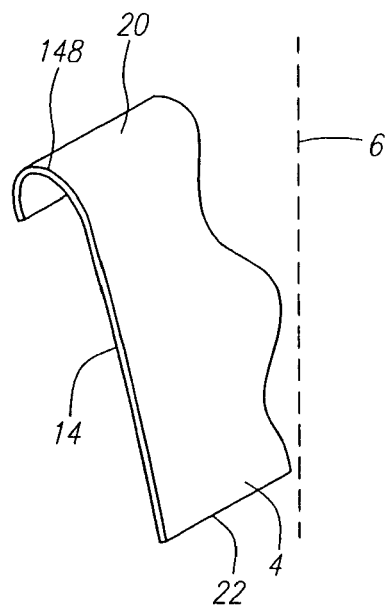

FIG. 47 illustrates a length of wall 4 with the engagement element 148, shaped as an open lip, on the leading edge 20. The engagement element 148 can be turned toward the longitudinal axis 6 and toward the trailing edge 22. FIG. 48 illustrates the engagement element 148 turned away from the longitudinal axis 6 and toward the trailing edge 22.

Figure 49:
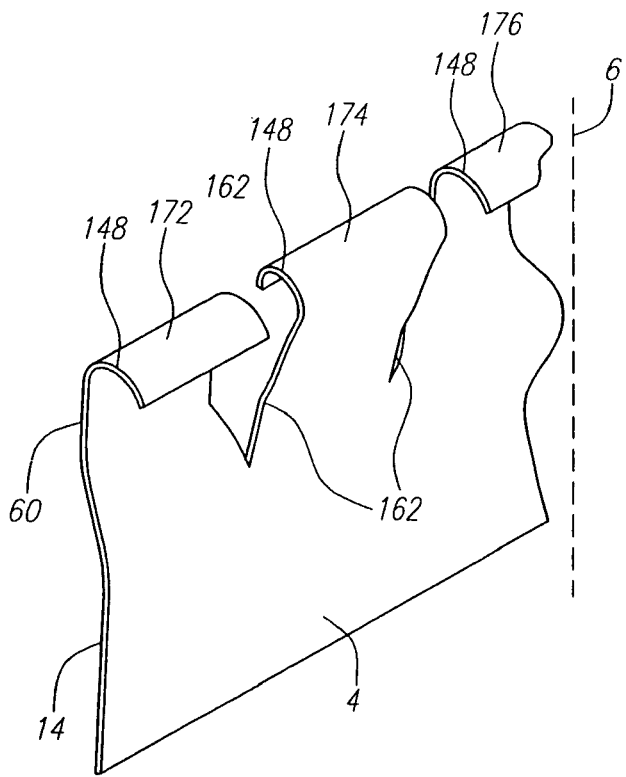
Figure 50:
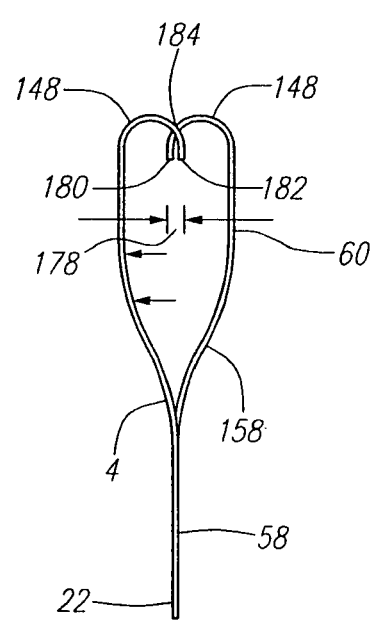

FIGS. 49 and 50 illustrate an embodiment of the first prosthesis 2 that can have a first length 172, a second length 174 and a third length 176. The lengths 172, 174 and 176 can be separated by cuts 162 in the wall 4. The engagement element 148 on the first length 172 and third length 176 can turn toward the longitudinal axis 6. The top and middle segments 60 and 158 of the first length 172 and the third length 176 can be bent away from the bottom segment 58 as shown by the arrows in FIG. 50. The top and middle segments 60 and 158 of the second length 174 can be similarly bent but in the opposite direction to the top and middle segments 60 and 158 of the first and third lengths 172 and 176. The engagement element 148 on the second length 174 can turn away from the longitudinal axis 6. A lip length 178 can be the length between a first lip edge 180 of the engagement element 148 on the first length 172 or third length 176 and a second lip edge 182 of the engagement element 148 on the second length 174. The lip length 178 can be small enough to form a seam, crease or seat 184 to aid in seating, receiving and engaging a second prosthesis.

FIG. 51 illustrates a length of the wall 4 that can have the lengths 172, 174 and 176. The engagement elements 148 on the first length 172 and third length 176 can turn away from the longitudinal axis 6. The engagement element 148 on the second length 174 can turn toward the longitudinal axis 6. The engagement element 148 can then engage a second prosthesis on both sides of the wall 4.

FIG. 52 illustrates an embodiment that can have springs 186. One segment of each spring 186 can be a latch 188. The springs 186 can have windings 190 around a rail 192 fixed under the engagement element 148. The springs 186 can also have retaining legs 194 pressed against the wall 4. The latches 188 can be biased to contract, as shown by arrows 196, against the wall 4. The latches 188 can be held in the uncontracted position shown in FIG. 52 by interference beams 198. The interference beams 198 can be directly or indirectly rigidly attached to each other at a proximal end (in the direction of arrows 200) to minimize the interference beams 198 from deflecting under the force, shown by arrows 196, from the latches 188. The interference beams 198 can be removed, as shown by arrows 200, allowing the latches 188 to contract, as shown by arrows 196, against, for example, the second prosthesis, once the second prosthesis is positioned within the reach of the latches 188.

Method of Making

The wall 4 can be made from methods known to one having ordinary skill in the art. For example, the wall 4 can be molded or machined. The engagement element 148, the corrugation and any other bends in the wall 4 can be formed (e.g., pressure formed), molded or machined into the wall 4 or bent into the metal with methods known to one having ordinary skill in the art.

The protrusions 26 and 28 and the receiving elements 32 and 34 (e.g., at the connection zone 118) can be fixed to the to the wall 4 or formed of the wall 4 by crimping, stamping, melting, screwing, gluing, welding, die cutting, laser cutting, electrical discharge machining (EDM) or a combination thereof. Cuts 162 and holes in the wall 4 can be made by die cutting, lasers or EDM.

Any part of the first prosthesis 2, or the first prosthesis 2 as a whole after assembly, can be coated by dip-coating or spray-coating methods known to one having ordinary skill in the art. One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating. The coatings can be thrombogenic or anti-thrombogenic. For example, coatings on the inside of the first prosthesis 2, the side facing the longitudinal axis 6, can be anti-thrombogenic, and coatings on the outside of the first prosthesis, the side facing away from the longitudinal axis 6, can be thrombogenic.

The first prosthesis 2 can be covered with a fabric, for example polyester (e.g., DACRON® from E. I. du Pont de Nemours and Company, Wilmington, Del.), polypropylene, PTFE, ePTFE, nylon, extruded collagen, silicone or combinations thereof. Methods of covering an implantable device with fabric are known to those having ordinary skill in the art.

Method of Use

Figure 53:
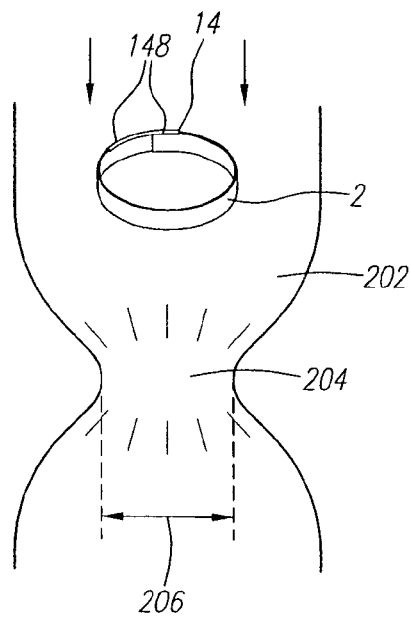
FIG. 53 is a cut-away view of an embodiment of positioning the prosthesis in an annulus with a solid view of the prosthesis.
Figure 54:
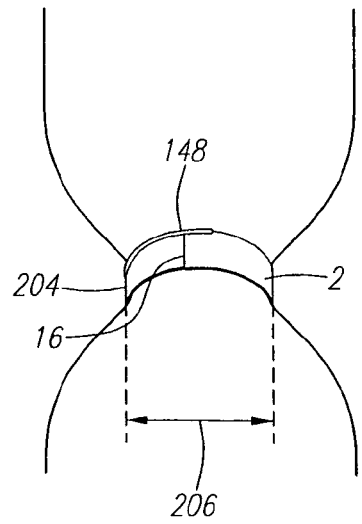
FIG. 54 is a cut-away view of an embodiment of positioning the prosthesis in an annulus.

The first prosthesis 2 can be introduced in an unexpanded state to an antechamber 202 adjacent to a targeted valve annulus 204 by methods known to one having ordinary skill in the art. FIG. 53 illustrates positioning and lowering, as shown by the arrows, the first prosthesis 2 to the annulus 204. Because of the collapsible and expandable nature of the first prosthesis 2, the procedure of implanting the first prosthesis 2 can be accomplished thorascopically, endoscopically and/or endoluminally. The first prosthesis 2 can be placed accurately enough into the annulus 204 so that the first prosthesis 2 does not block vessel openings in chambers neighboring the annulus 204 (e.g., the openings for the coronary vessels) and does not fall out of the annulus 204 (e.g., into a chamber of the heart, a ventricle for example). The annulus 204 can have an initial annulus diameter 206. FIG. 54 illustrates positioning and seating the first prosthesis 2.

Figure 55:
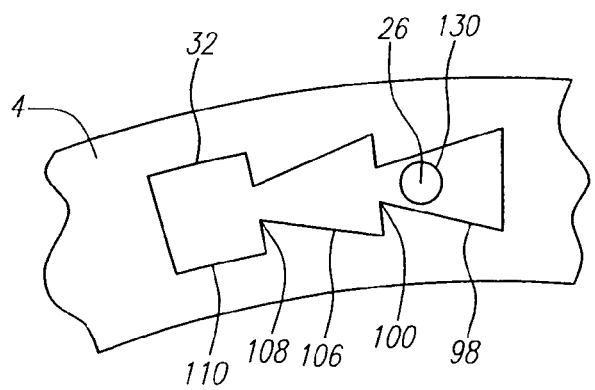
FIGS. 55 and 56 illustrate various embodiments of the protrusions and receiving elements when the prosthesis is not expanded.
Figure 56:
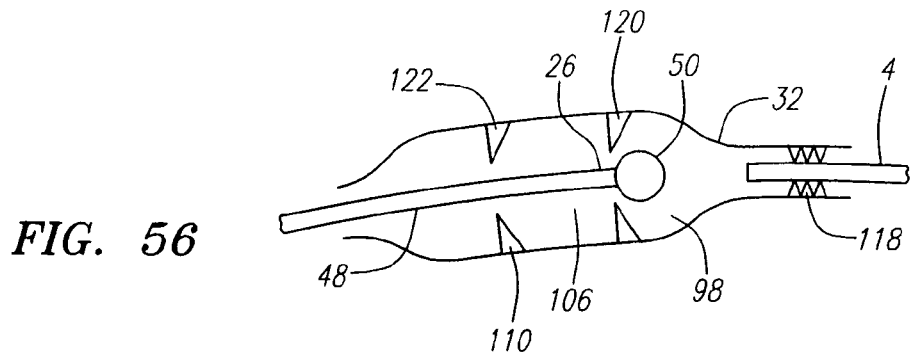

When the first prosthesis 2 is completely unexpanded, the protrusion 26 and the receiving element 32 can be aligned as illustrated in FIGS. 55 and 56. As shown in FIG. 55, the extension 130 can be located in the first setting position 98. As shown in FIG. 56, the ball 50 can be located in the first setting position 98.

Figures 57, 64:
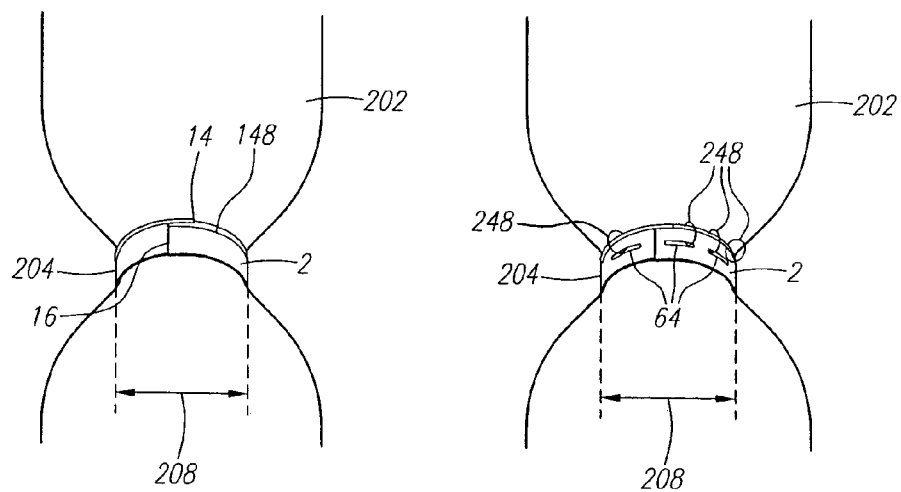
FIG. 57 is a cut-away view of an embodiment of expanding the prosthesis.
FIG. 64 is a cut-away view of fixturing the prosthesis to a biological mass.

The first prosthesis 2 can be circumferentially expanded, as illustrated by the arrows in FIG. 57. The prosthesis can have an expanded annulus diameter 208. The expanded annulus diameter 208 can be from about 5 mm (0.2 in.) to about 40 mm (1.6 in.), depends on the size of the initial annulus diameter 206, and can be influenced by other anatomy, anomalies (e.g., narrowing, stenosis) and age (e.g., pediatric sizing). An expansion tool 210 can be used to expand the first prosthesis 2. Examples of the expansion tool 210 include a balloon, back sides of a clamp jaws, or a flexible plug assembly as shown in FIGS. 58-61. Another example of the expansion tool 210 is disclosed in U.S. Pat. No. 5,984,959 to Robertson et al. which is herein incorporated by reference in its entirety.

Figure 58:
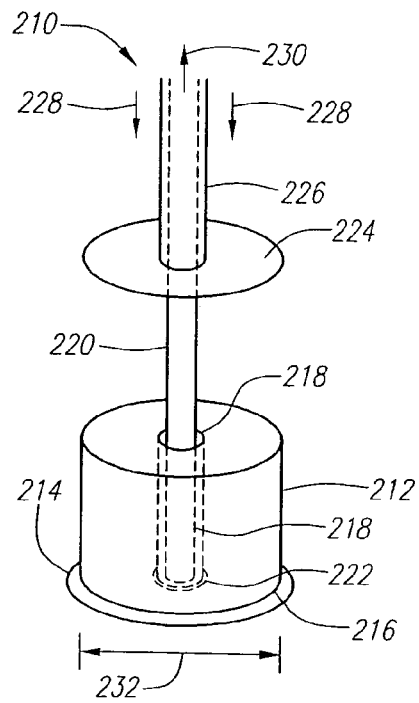
FIGS. 58 and 59 illustrate an embodiment of an expansion tool.

FIG. 58 illustrates a flexible plug 212 that can be cylindrical and have a static plate 214 on a first side 216. The plug 212 can be made from polymers, for example polyurethane or silicone. The plug 212 can have a hole 218 in the center of the plug 212. A rigid inner tube 220 can pass through the hole 218 and be tied into a knot or pull against a washer 222 on the first side 216. A squeeze plate 224 can be fixedly attached to an end of a rigid outer tube 226. The outer tube 226 can be larger than the inner tube 220, and the inner tube 220 can slide through the outer tube 226. A force in the direction of the plug 212 can be applied to the outer tube 226, as shown by arrows 228. A force in the direction away from the plug 212 can be applied to the inner tube 220, as shown by arrows 230. The plug can have a resting diameter 232 when no forces are applied.

Figure 59:
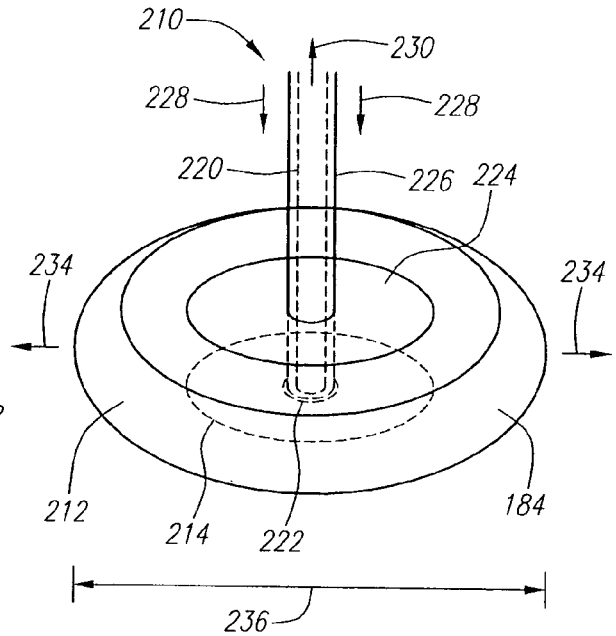

Once the forces shown by the arrows 228 and 230 are applied to the plug 212, the plug 212 can deform away from the tubes 220 and 226, as shown by arrows 234 and illustrated in FIG. 59. Once deformed, the plug 212 can have an expanded diameter 236. The resting diameter 232 and the expanded diameter 236 can be sized appropriately to the dimensions of the first prosthesis 2. The deformation of the plug 212 can also create forces in the same direction as the arrows 234. When the forces shown by the arrows 228 and 230 are removed, the plug 212 can return to the shape shown in FIG. 58.

Figure 60:
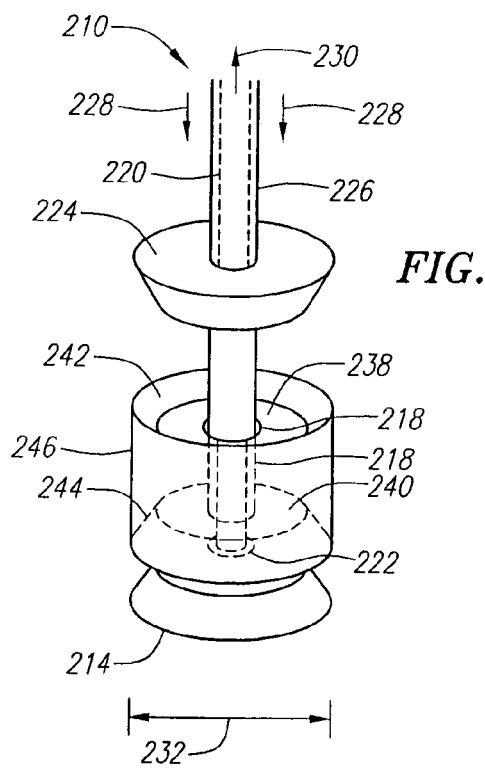
FIGS. 60 and 61 illustrate another embodiment of an expansion tool.
Figure 61:
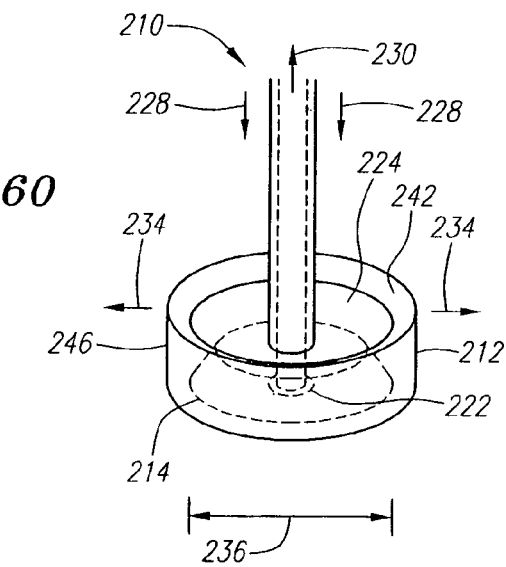

FIG. 60 illustrates another embodiment of the plug 212. The plug 212 can have a recessed top surface 238 and a recessed bottom surface 240. A top perimeter 242 and a bottom perimeter 244 can be angled from the recessed surfaces 238 and 240 to meet a wall 246 of the plug 212. The squeeze plate 224 and the static plate 214 can both be conically or partially conically shaped to fit the perimeters 242 and 244 of the plug 212. As shown in FIG. 61, when the forces shown by the arrows 228 and 230 are applied, the plug wall 246 can expand radially and maintain a flat surface.

Figure 62:
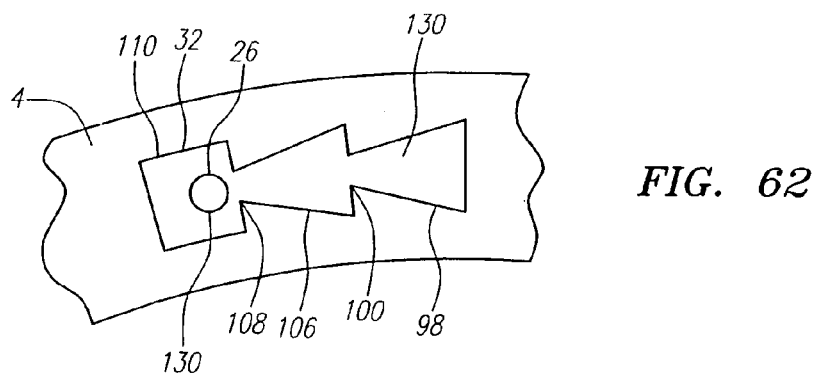
FIGS. 62 and 63 illustrate various embodiments of the protrusions and receiving elements when the prosthesis is expanded.
Figure 63:
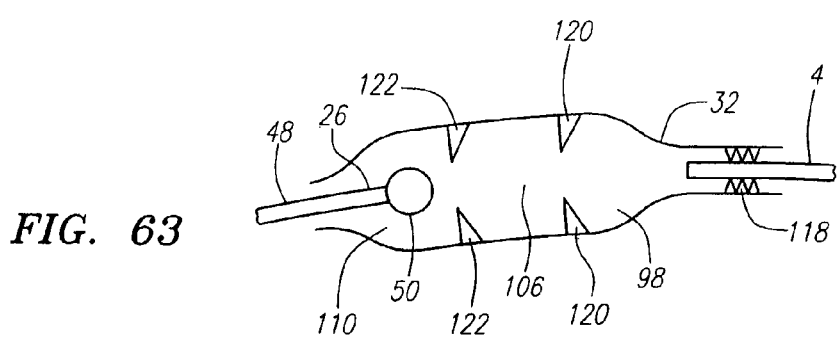

When the first prosthesis 2 is completely expanded, the protrusion 26 and the receiving element 32 can be aligned as illustrated in FIGS. 62 and 63. As shown in FIG. 62, the extension 130 can be located in the final stop position 110. As shown in FIG. 63, the ball 50 can be located in the final stop position 110. The interference fit caused by the stop angle 116 and neck width 104 of the second neck 108 can prevent the protrusion 26 from re-entering the second setting position 106. In addition, when expanded the first prosthesis frictionally engages the annulus, expanding the annulus diameter. When expanded, the first prosthesis 2 can also trap vascular plaque between the wall 4 and the perimeter of the annulus 204. The first prosthesis 2 can also be partially expanded, forcing the protrusion 26 into the second setting position 106.

Fixturing devices 248 can be used to fix the first prosthesis 2 through the fixturing device connectors 88 to the biological mass of the annulus 204, as shown in FIG. 64. Examples of fixturing devices 88 are sutures, clips, staples, pins and combinations thereof.

Figure 65:
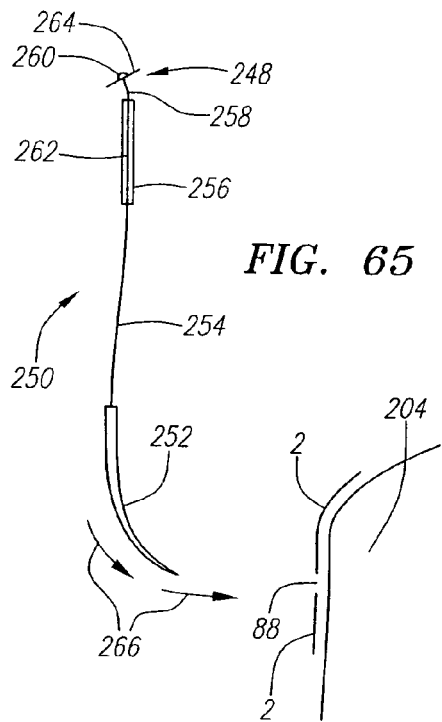
FIGS. 65-68 illustrate an embodiment of a method and assembly for fixturing the prosthesis to a biological mass.
Figure 66:
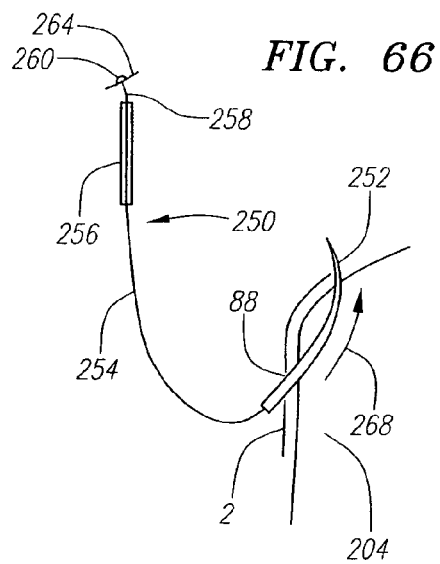
Figure 67:
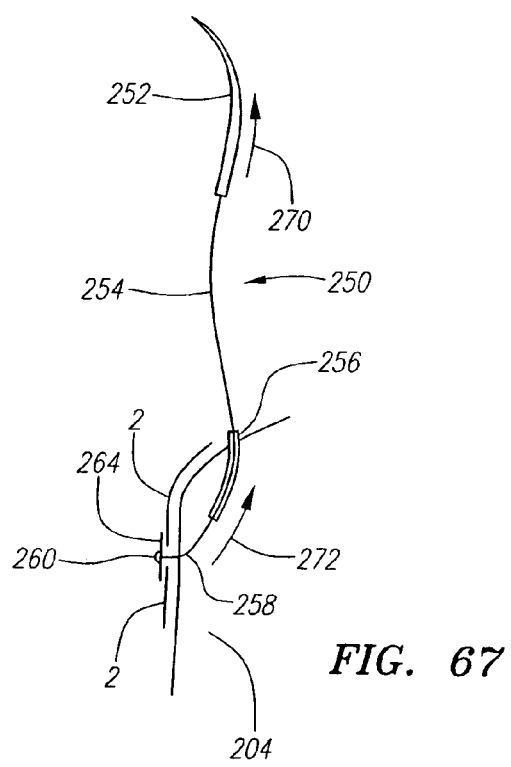
Figure 68:
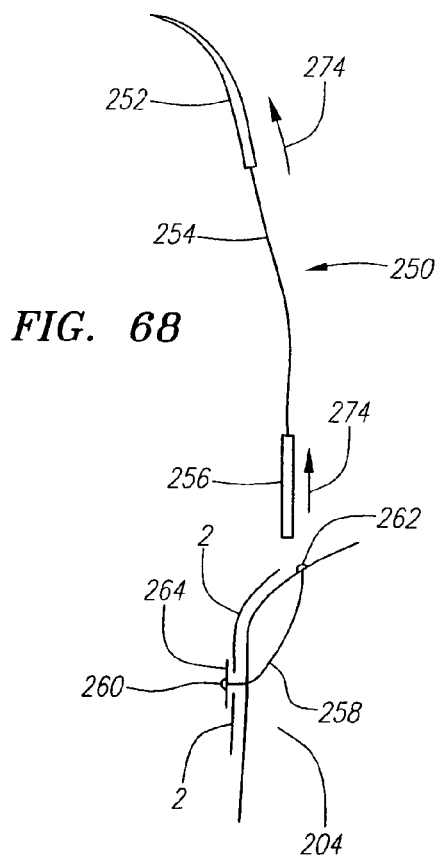

FIGS. 65-68 illustrate one embodiment of a method of fixing the first prosthesis 2 to the annulus 204. FIG. 65 illustrates an embodiment of a fixturing device assembly 250. The fixturing device assembly 250 can have a needle 252. The needle 252 can be curved or have a curved tip. The needle 252 can also be attached at a proximal end to a distal end of a line 254. The proximal end of the needle 252 can also be attached directly to the can 256 without the line 254 or formed as the can 256. A proximal end of the line 254 can be attached to a can 256. The can 256 can be a flexible cylindrical storage device, for example a coil. The can 256 can removably hold the fixturing device 248. The fixturing device 248 can have a fixturing element 258, for example a wire or fiber. The fixturing element 258 can have a ball 260 at a first end and a radially expandable portion 262 at a second end. The fixturing device 248 can also have a pledget 264 on the fixturing element 258 between the ball 260 and the expandable portion 262.

The fixturing device assembly 250 can be positioned so the needle 252 is adjacent to the fixturing device connector 88, as shown by arrows 266. The needle 252 can then be pushed through the fixturing device connector 88 and the annulus 204, as shown by arrow 268 in FIG. 66. The needle 252 can then be pulled away from the annulus 204, as shown by arrow 270 in FIG. 67. The can 256 can follow the path of the needle 252 through the annulus 204, as shown by arrow 272. The pledget 264 can also be larger than the fixturing device connector 88, and the pledget 264 can provide an interference fit against the fixturing device connector 88. The needle 252 can continue to be pulled away from the annulus 204, pulling the can 256 out of the annulus 204, as shown by arrow 274 in FIG. 68. The interference fit of the pledget 264 against the fixturing device connector 88 can provide a resistive force holding the fixturing device 248 and causing the fixturing element 258 to slide out of the can 256 as the needle 252 is pulled away from the annulus 204. The radially expandable portion 262 can then radially expand, thereby causing the first prosthesis 2 and the annulus 204 to be fixed between the pledget 264 and the radially expandable portion 262.

The inner surface of the can 256 can be designed—for example by coiling, corrugation, or other roughening—to adjust the friction between the inner surface of the can 256 and the fixturing device 248. This friction can influence the amount of resistive force necessary to remove the fixturing device 248 from the can 256. The resistive force can be larger than about the force necessary to have the fixturing device 248 fall out of the can 256 before the fixturing device 248 has passed through the annulus 104. The resistive force can also be less than about the force necessary to deform the pledget 264 sufficient to pull the pledget 256 through the fixturing device connector 88. The resistive force can be, for example, about 1.1 N (0.25 lbs.).

A second prosthesis 68 can then be positioned on the engagement element 148, as shown by the arrows in FIG. 69. Once seated on the engagement element 148, the second prosthesis 68 can then be engaged by the first prosthesis 2, as shown in FIG. 70. Examples of second prostheses 68 include a connection adapter and a heart valve crown with leaflets 276, for example, U.S. Pat. No. 6,371,983 to Lane which is herein incorporated by reference in its entirety.

Figure 71:
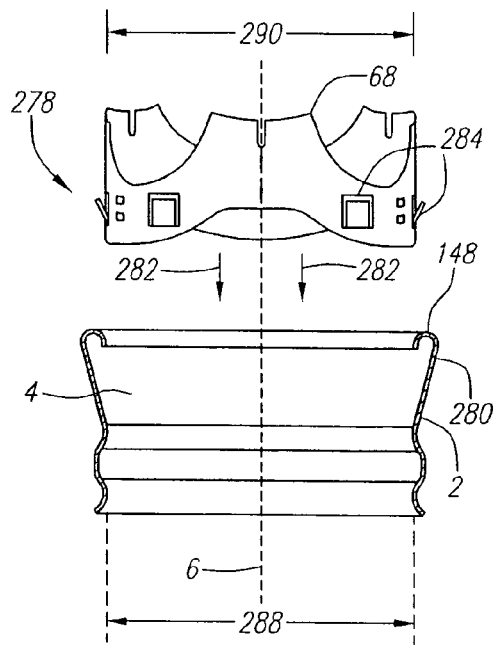
FIGS. 71-77 are exploded views of various embodiments of attaching the second prosthesis to the first prosthesis.
Figure 72:
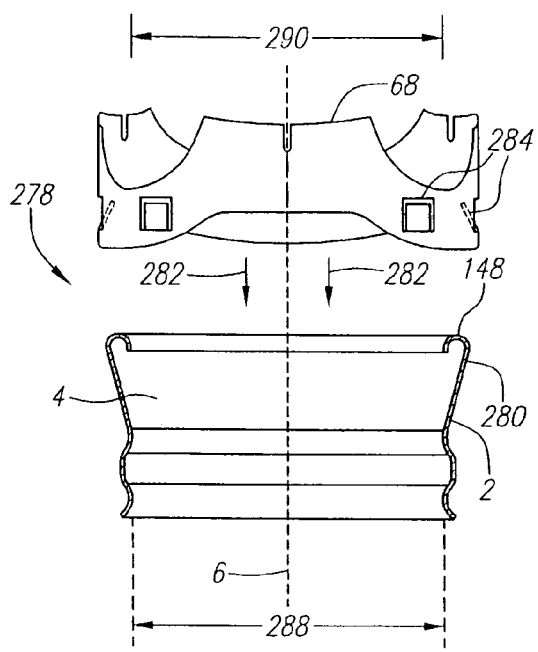

FIG. 71 illustrates another embodiment of the heart valve assembly 278 with the second prosthesis 68. The first prosthesis 2 can have a tapered wall 280 to provide a longitudinal stop and to guide insertion of the second prosthesis 68 into the first prosthesis 2, as shown by arrows 282. The tapered wall 280 can also push back the annulus 204, maintaining the expanded annulus diameter 208 when the second prosthesis 68 is engaged in the first prosthesis 2. The second prosthesis 68 can have spring lock tabs 284 to fix to the engagement element 148. The spring lock tabs 284 can angle outwardly from the longitudinal axis 6. The first and second prostheses 2 and 68 can have first and second prosthesis diameters 288 and 290, respectively. The first prosthesis diameter 288 can be larger than the second prosthesis diameter 290. FIG. 72 illustrates the embodiment of the heart valve assembly 278 of FIG. 71, however the second prosthesis diameter 290 can be larger than the first prosthesis diameter 288, and the spring lock tabs 284 can angle inwardly toward the longitudinal axis 6. The first prosthesis 2 and the second prosthesis 68 act to maintain the expanded annular lumen diameter 208.

Figure 73:
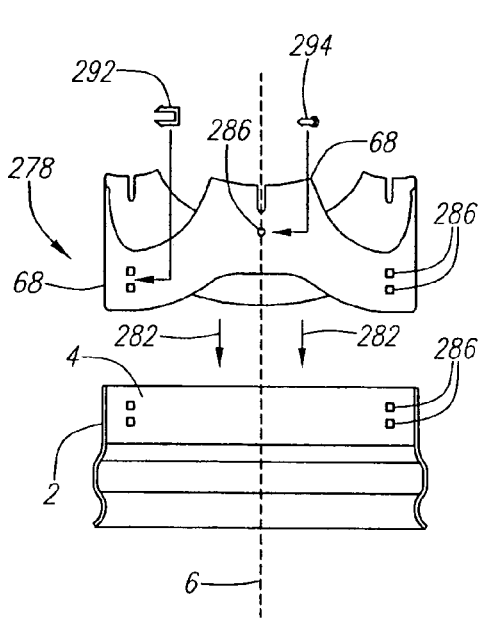

FIG. 73 illustrates another embodiment of the heart valve assembly 278 with a second prosthesis 68 that can have fixation points 286 that align with fixation points 286 on the first prosthesis 2 to allow insertion of sutures, grommets, clips 292 or pins 294 through the aligned fixation points 286 to fix the first prosthesis 2 to the second prosthesis 68.

Figure 74:
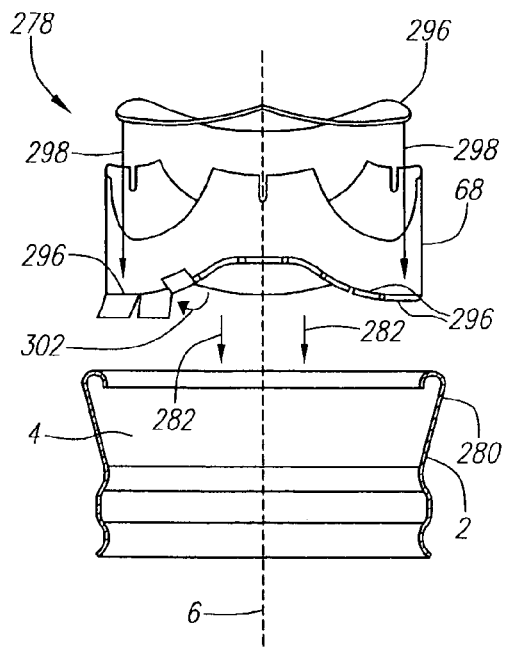

FIG. 74 illustrates another embodiment of the heart valve assembly 278 with a multi-lobed stiffening ring 296 that can be placed near the edge of the second prosthesis 68 as shown by arrows 298. The second prosthesis 68 can have several flaps 300. The flaps 300 can wrap around the stiffening ring 296, as shown by arrows 302. The wrapped stiffening ring 296 can increase the rigidity of the second prosthesis 68 and can engage the engagement element 148.

Figure 75:
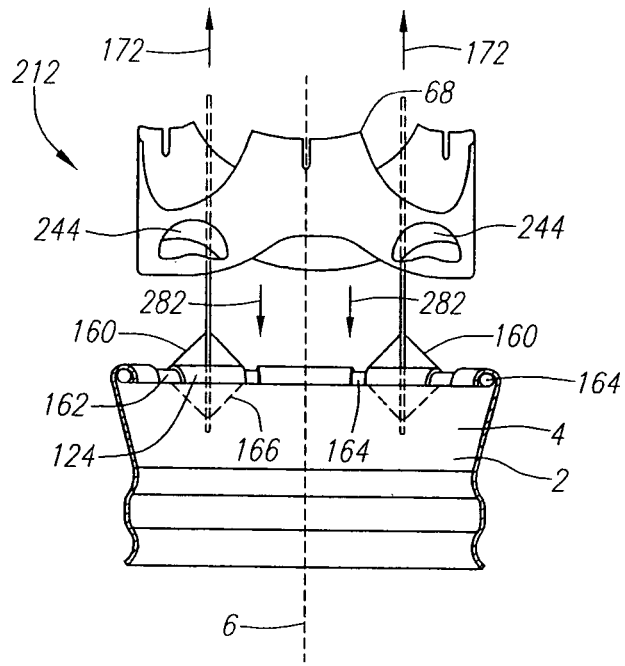

FIG. 75 illustrates yet another embodiment of the heart valve assembly 278 with an embodiment of the first prosthesis 2 equivalent to the embodiment in FIG. 52. The second prosthesis 68 can have latch openings 304 to receive the latches 188. When the second prosthesis 68 is lowered into the first prosthesis 2, the interference beams 198 can be removed, as shown by arrows 200. The latches 188 can then contract onto the latch openings 304.

Figure 76:
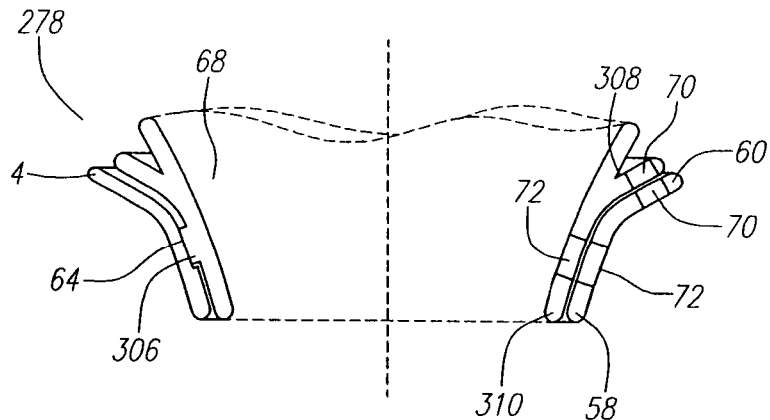
Figure 77:
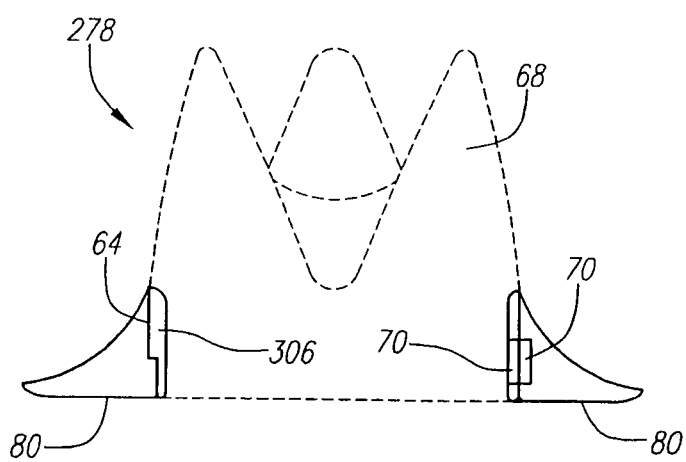

FIG. 76 illustrates an embodiment of the heart valve assembly 278 with an embodiment of the first prosthesis 2 equivalent to the embodiment in FIGS. 11 and 12. The second prosthesis can have a rib 306 to fit within the groove 64. The second prosthesis 68 can also have an upper arm 308 that can have a top magnet 70 and a lower arm 310 that can have a bottom magnet 72. The magnets 70 and 72 in the second prosthesis 68 can have polarities opposite of the polarities of the corresponding magnets 70 and 72 in the first prosthesis 2. FIG. 77 illustrates an embodiment of the heart valve assembly 278 with an embodiment of the first prosthesis equivalent to the embodiment in FIGS. 13 and 14.

FIG. 78 illustrates an embodiment of the heart valve assembly 278 with an adapter 312 connecting the second prosthesis 68 to the first prosthesis 2. The adapter 312 can have spring lock tabs 284 to fix to the engagement element 148, and the adapter 312 can have a stop ridge 314 to position the adapter 312 against the wall 4.

The adapter 312 can also have fixation points 286 that align with other fixation points 286 on the second prosthesis 68 to allow insertion of sutures, grommets, clips, pins, or the fixturing devices 248, through the aligned fixation points 286 to fix the adapter 312 to the second prosthesis 68. The second prosthesis 68 can also be lowered into the top of the adapter 312 as shown by arrow 316. The adapter 312 can attach to the inside or outside of the first or second prosthesis 2 or 68 depending on the dimensions and the orientation of the attachment apparatus (e.g., unidirectional clips).

The adapter 312 can also have multiple shapes of cross-sections, as shown in FIGS. 79 and 80. As shown in FIG. 79, cross-section C-C can have three lobes 318 and three scallops 320. One scallop 320 can be between each lobe 318. Cross-section C-C can be the same as the cross-section of the second prosthesis 68 where the second prosthesis 68 engages the adapter 312. As shown in FIG. 80, cross-section D-D can be circular. Cross-section D-D can be the same as the cross-section of the first prosthesis 2 where the first prosthesis 2 engages the adapter 312.

Figure 81:
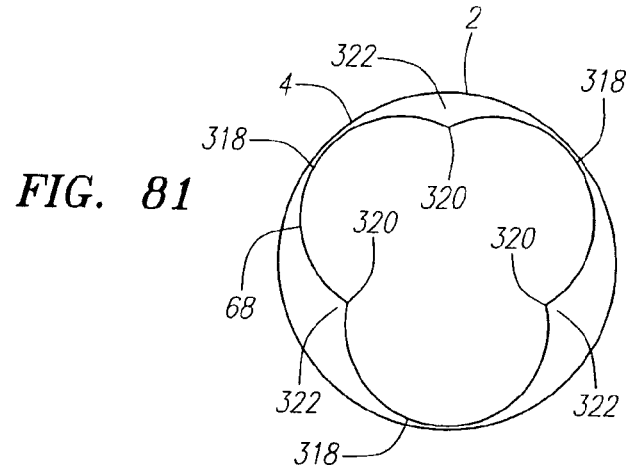
FIG. 81 is a top view of an embodiment of the first prosthesis with the second prosthesis attached thereto.

FIG. 81 illustrates a second prosthesis 68 received by a first prosthesis 2. The second prosthesis 68 can have three lobes 318. The second prosthesis can have a scallop 320 between each two lobes 318. The scallop gap 322 between each scallop 320 and the wall 4 can be covered by a fabric during use of the prostheses 2 and 68.

Figure 82:
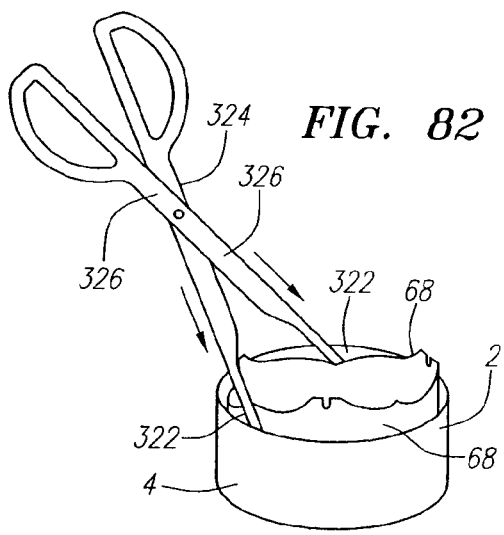
FIGS. 82-84 illustrate an embodiment of a method of removing the second prosthesis from the first prosthesis.
Figure 84:
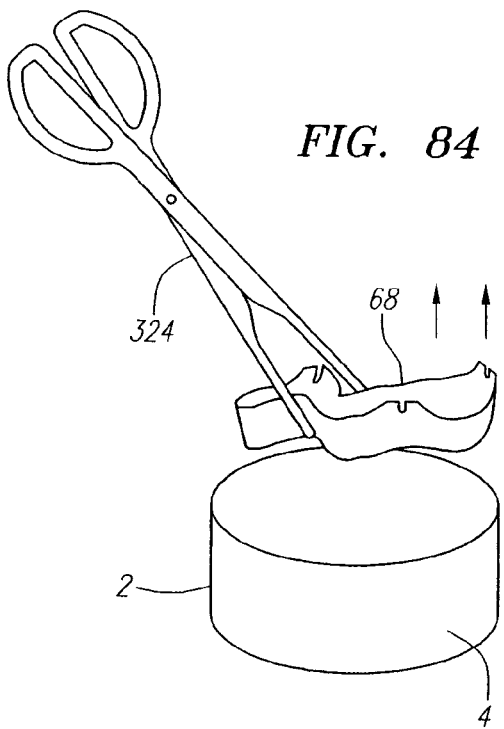
Figure 83:
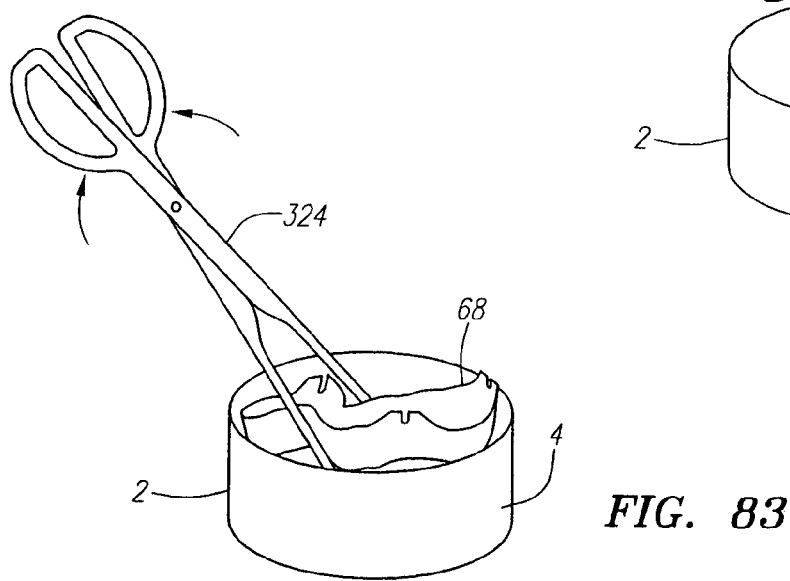

FIG. 82 illustrates that a lever device 324, for example a clamp or scissors, can be forced, as shown by arrows, into the scallop gap 322. As illustrated in FIG. 83, once legs 326 of the lever device 324 are placed next to two scallops 320, the lever device 324 can be squeezed, as shown by arrows, thereby crushing the second prosthesis 68 and separating it from the first prosthesis 2. As illustrated in FIG. 84, the second prosthesis 68 can be removed from the first prosthesis 2, as shown by arrows, once the second prosthesis 68 is separated from the first prosthesis 2. Once the second prosthesis 68 is removed, a new second prosthesis 68 can be added as described above. Leaflet failure can be fixed easily and inexpensively by implanting a new second prosthesis 68. Circumferential expansion of the first prosthesis 2 and replacement of the second prosthesis 68 to account for pediatric expansion of the valve can also be performed easily and inexpensively.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

We claim:

1. A biologically implantable system for a heart valve, comprising:
a first prosthesis comprising an annular ring implantable directly and independently into an annulus of a heart, the first prosthesis comprising a circumference and a fabric covering, the annular ring having a circular latitudinal cross-section perpendicular to a central longitudinal axis;

a second prosthesis comprising a heart valve crown, the second prosthesis further comprising a circumference including a fabric covering thereon, the crown comprising an annular frame carrying leaflets, the frame having a latitudinal cross-section in a plane perpendicular to the central longitudinal axis defining multiple lobes separated by scallops, the scallops being disposed closer to the central longitudinal axis within the plane than the lobes; and at least one engagement element disposed on the circumferences of the first and second prostheses that self-engage one another when the second prosthesis is inserted into engagement with the first prosthesis after the first prosthesis is implanted within an annulus of a heart.

2. The system of claim 1, further comprising cooperating elements on the first and second prostheses that angularly align the second prosthesis with the first prosthesis when the second prosthesis is inserted into engagement with the first prosthesis.

3. The system of claim 2, wherein the cooperating elements comprise a rib and groove on the first and second prostheses, the rib fitting within the groove when the second prosthesis is inserted into engagement with the first prosthesis.

4. The system of claim 1, wherein the at least one engagement element comprises a plurality of lips disposed around the circumference of the first prosthesis and a plurality of spring lock tabs disposed around the circumference of the second prosthesis.

5. The system of claim 1, wherein the first prosthesis comprises a tapered wall to guide the second prosthesis during insertion into the first prosthesis.

6. The system of claim 1, wherein the circumference of the second prosthesis defines a shape including three lobes.

7. A biologically implantable system for a heart valve, comprising:
a first prosthesis implantable within an annulus of a heart, the first prosthesis comprising a circumference;
a second prosthesis comprising a heart valve crown, the second prosthesis comprising a circumference;
a plurality of engagement elements disposed around the circumference of the second prosthesis, the engagement elements comprising angled distal surfaces;
a plurality of elements disposed around the circumference of the first prosthesis that contact the angled distal surfaces of the engagement elements when the second prosthesis is inserted into the annulus into engagement with the first prosthesis to accommodate the engagement elements self-engaging with the plurality of elements on the first prosthesis; and
cooperating elements on the first and second prostheses that angularly align the second prosthesis with the first prosthesis when the second prosthesis is inserted into engagement with the first prosthesis,
wherein the engagement elements comprise tabs extending from the second prosthesis at an angle to defined the angled distal surfaces, the tabs being deflectable when the angled distal surfaces contact the plurality of elements on the first prosthesis to accommodate the tabs self-engaging with the plurality of elements on the first prosthesis,
wherein the plurality of elements on the first prosthesis comprise a plurality of lips for slidably engaging the angled distal surfaces of the plurality of tabs, the lips defining pockets for receiving the plurality of tabs therein to prevent separation of the first and second prostheses.

8. The system of claim 7, wherein the cooperating elements comprise a rib and groove on the first and second prostheses, the rib fitting within the groove when the second prosthesis is inserted into engagement with the first prosthesis.

9. The system of claim 7, wherein the cooperating elements comprise a plurality of magnets disposed around the circumferences of the first and second prostheses.

10. The system of claim 7, wherein the first prosthesis comprises a tapered wall to guide the second prosthesis during insertion into the first prosthesis.

11. The system of claim 7, wherein the second prosthesis further comprises three lobes, and wherein the circumference of the second prosthesis comprises a fabric covering extending around the circumference.

12. A biologically implantable system for a heart valve, comprising:
a first annular prosthesis implantable within an annulus of a heart, the first prosthesis comprising an annular ring having a circular latitudinal cross-section perpendicular to a central longitudinal axis and a fabric covering;
a second prosthesis separate from the first prosthesis and comprising a heart valve crown, the crown comprising an annular frame carrying leaflets, the frame having a latitudinal cross-section in a plane perpendicular to the central longitudinal axis defining multiple lobes separated by scallops, the scallops being disposed closer to the central longitudinal axis within the plane than the lobes;
a plurality of engagement elements disposed around the circumferences of the first and second prostheses that self-engage one another when the second prosthesis is inserted into engagement with the first prosthesis; and
cooperating elements on the first and second prostheses separate from the plurality of engagement elements, said cooperating elements capable of angularly aligning the second prosthesis with the first prosthesis and preventing rotation of the second prosthesis with respect to the first prosthesis as the second prosthesis is inserted into engagement with the first prosthesis after the first prosthesis is implanted within an annulus of a heart.

13. A biologically implantable system for a heart valve, comprising:
a first annular prosthesis implantable within an annulus of a heart, the first prosthesis comprising a circumference and a fabric covering;
a second prosthesis separate from the first prosthesis and comprising a heart valve crown, the second prosthesis comprising a circumference;
a plurality of engagement elements disposed around the circumferences of the first and second prostheses that self-engage one another when the second prosthesis is inserted into engagement with the first prosthesis; and
cooperating elements on the first and second prostheses separate from the plurality of engagement elements, said cooperating elements capable of angularly aligning the second prosthesis with the first prosthesis and preventing rotation of the second prosthesis with respect to the first prosthesis as the second prosthesis is inserted into engagement with the first prosthesis after the first prosthesis is implanted within an annulus of a heart,
wherein the cooperating elements comprise a rib and groove on the first and second prostheses, the rib fitting within the groove as the second prosthesis is inserted into engagement with the first prosthesis in a predetermined angular orientation to longitudinally align the second prosthesis with the first prosthesis.

14. The system of claim 12, wherein the circumference of the second prosthesis defines a multiple lobed shape in a latitudinal cross-section perpendicular to a central longitudinal axis including three lobes.

15. The system of claim 1, wherein the annular ring has a tapered wall configured to push back the annulus when the first prosthesis is inserted into the annulus.

16. The system of claim 1, wherein the first prosthesis comprises a top segment, a bottom segment, and a longitudinal axis substantially perpendicular to the circumference, at least one of the top and bottom segments defining an angle with the longitudinal axis such that the top segment has an outer circumference larger than the bottom segment.

17. The system of claim 16, wherein the first prosthesis comprises a joint angle between the top segment and the bottom segment.

18. The system of claim 16, wherein the top segment defines an angle with the longitudinal axis that is greater than the bottom segment.

19. The system of claim 1, further comprising a plurality of fixturing devices configured to be inserted through a portion of the first prosthesis for securing the first prosthesis to the annulus before the second prosthesis is introduced into the annulus.

20. The system of claim 1, wherein the at least one engagement element comprises means for snap-fitting the second prosthesis to the first prosthesis.

21. The system of claim 1, wherein the at least one engagement element comprises a plurality of connectors for snap-fitting the second prosthesis to the first prosthesis.

22. The system of claim 12, wherein the first prosthesis comprises a top segment, a bottom segment, and a longitudinal axis substantially perpendicular to the circumference, at least one of the top and bottom segments defining an angle with the longitudinal axis such that the top segment has an outer circumference larger than the bottom segment.

23. The system of claim 12, wherein the cooperating elements comprise a plurality of connectors for snap-fitting the second prosthesis to the first prosthesis.

24. A biologically implantable system for a heart valve, comprising:
   a first annular prosthesis implantable into an annulus within a heart, the first prosthesis including a wall defining a circumference and a central longitudinal axis substantially perpendicular to the circumference, at least a portion of the wall being angled away from the longitudinal axis, the wall having a circular latitudinal cross-section perpendicular to the central longitudinal axis and being foldable into an unexpanded state during delivery including one or more folds and resiliently expandable radially for increasing the circumference and for engaging the tissue annulus;
   a second annular prosthesis comprising a valve;
   at least one engagement element on the first and second prostheses that engage one another when the second prosthesis is inserted into engagement with the first prosthesis after the first prosthesis is implanted within an annulus of a heart;
   wherein the at least one engagement element comprises means for snap-fitting the second prosthesis to the first prosthesis.

25. The system of claim 24, the first prosthesis comprising a top annular segment and a bottom annular segment, at least one of the top and bottom segments defining an angle with the longitudinal axis such that the top segment has an outer circumference larger than the bottom segment.

26. The system of claim 25, wherein the first prosthesis comprises a joint angle between the top segment and the bottom segment.

27. The system of claim 25, wherein the top segment defines an angle with the longitudinal axis that is greater than the bottom segment.

28. The system of claim 24, wherein the second prosthesis comprises a circumferential multiple lobed shape in a latitudinal cross-section perpendicular to the central longitudinal axis that includes a scallop between adjacent lobes.

29. The system of claim 28, wherein the circumferential shape of the second prosthesis has three lobes.

30. The system of claim 24, further comprising a plurality of fixturing devices configured to be inserted through a portion of the first prosthesis for securing the first prosthesis to the annulus before the second prosthesis is introduced into the annulus.

31. The system of claim 24, wherein the at least one engagement element comprises a plurality of connectors for snap-fitting the second prosthesis to the first prosthesis.

32. The system of claim 24, wherein the first annular prosthesis comprises a metal ring.

33. The system of claim 1, wherein the annular ring is foldable into an unexpanded state during delivery and is resiliently expandable radially for engaging the tissue annulus.

34. The system of claim 2, wherein the cooperating elements on the first and second prostheses are separate from the plurality of engagement elements.

35. The system of claim 12, wherein the first prosthesis comprises a wall defining the circumference and a central longitudinal axis substantially perpendicular to the circumference, the wall having a circular latitudinal cross-section perpendicular to the central longitudinal axis and being foldable into an unexpanded state during delivery and resiliently expandable radially for increasing the circumference for engaging the tissue annulus.

36. The system of claim 12, wherein the cooperating elements are configured to longitudinally align the second prosthesis with the first prosthesis as the second prosthesis is inserted into engagement with the first prosthesis in a predetermined angular orientation.

37. A biologically implantable system for a heart valve, comprising:
   a first prosthesis comprising an annular ring implantable directly and independently into an annulus of a heart and a fabric covering, the annular ring having a circular latitudinal cross-section perpendicular to a central longitudinal axis and being foldable into an unexpanded state during delivery including one or more folds and resiliently expandable radially for increasing the circumference and for engaging the tissue annulus;
   a second prosthesis comprising a heart valve crown comprising an annular frame carrying leaflets, the frame having a latitudinal cross-section in a plane perpendicular to the central longitudinal axis defining multiple lobes separated by scallops, the scallops being disposed closer to the central longitudinal axis within the plane than the lobes; and
   a plurality of engagement elements spaced apart from one another about a circumference of the first prosthesis and a corresponding plurality of engagement elements spaced apart from one another about a circumference of the frame of the crown that self-engage one another when the second prosthesis is inserted into engagement with the first prosthesis after the first prosthesis is implanted within an annulus of a heart.

* * * * *